(12) United States Patent
Chawla

(10) Patent No.: US 12,311,090 B2
(45) Date of Patent: May 27, 2025

(54) EXTRACORPOREAL BLOOD TREATMENT SYSTEMS AND METHODS EMPLOYING BATCH PROCESSING

(71) Applicant: STAVRO MEDICAL, INC., Martinez, CA (US)

(72) Inventor: Lakhmir Singh Chawla, Martinez, CA (US)

(73) Assignee: STAVRO MEDICAL, INC., Martinez, CA (US)

( * ) Notice: Subject to any disclaimer, the term of this patent is extended or adjusted under 35 U.S.C. 154(b) by 522 days.

(21) Appl. No.: 17/695,701

(22) Filed: Mar. 15, 2022

(65) Prior Publication Data

US 2022/0249756 A1    Aug. 11, 2022

Related U.S. Application Data

(63) Continuation-in-part of application No. PCT/US2020/064110, filed on Dec. 9, 2020.
(Continued)

(51) Int. Cl.
*A61M 1/30* (2006.01)
*A61M 1/16* (2006.01)

(52) U.S. Cl.
CPC .......... *A61M 1/301* (2014.02); *A61M 1/1605* (2014.02); *A61M 1/1694* (2013.01);
(Continued)

(58) Field of Classification Search
CPC ...... A61M 1/30; A61M 1/301; A61M 1/3603; A61M 1/3616; A61M 2205/3334
See application file for complete search history.

(56) References Cited

U.S. PATENT DOCUMENTS

| 4,599,165 A | 7/1986 | Chevallet |
| 5,227,049 A | 7/1993 | Chevallet et al. |

(Continued)

FOREIGN PATENT DOCUMENTS

| DE | 19633657 C1 | 11/1997 |
| EP | 2720733 B1 | 9/2017 |

(Continued)

OTHER PUBLICATIONS

EP Appln. No. 20899971.4, Extended European Search Report, May 3, 2024, 9 pages.
(Continued)

*Primary Examiner* — Bradley R Spies
(74) *Attorney, Agent, or Firm* — Kilpatrick Townsend & Stockton LLP

(57) ABSTRACT

Disclosed are methods and systems for a body-fluid (e.g., blood) treatment. The methods and systems include (a) conveying a volume of body-fluid (e.g., blood) via a first conduit from a vascular access of a patient to a blood chamber at a first flow rate, the first conduit having only a single lumen; (b) conveying the body-fluid (e.g., blood) from the blood chamber through a filtration device at a second flow rate to perform an extracorporeal treatment on the blood and returning the treated blood to the blood chamber; and (c) returning the body-fluid (e.g., blood) from the blood chamber to the vascular access of the patient at a third flow rate via the first conduit, wherein the second flow rate is decoupled from both the first and third flow rates.

20 Claims, 9 Drawing Sheets

Related U.S. Application Data

(60) Provisional application No. 63/164,202, filed on Mar. 22, 2021, provisional application No. 63/057,129, filed on Jul. 27, 2020, provisional application No. 62/947,312, filed on Dec. 12, 2019.

(52) U.S. Cl.
CPC ........... *A61M 2205/3334* (2013.01); *A61M 2205/3379* (2013.01); *A61M 2205/3393* (2013.01)

(56) References Cited

U.S. PATENT DOCUMENTS

| | | | |
|---|---|---|---|
| 5,318,511 | A | 6/1994 | Riquier et al. |
| 2004/0054320 | A1 | 3/2004 | Kissinger et al. |
| 2005/0205476 | A1 | 9/2005 | Chevallet et al. |
| 2011/0137224 | A1 | 6/2011 | Ibragimov |
| 2011/0178452 | A1 | 7/2011 | Kopperschmidt |
| 2014/0074007 | A1 | 3/2014 | Mcneil |
| 2014/0378893 | A1* | 12/2014 | Tsyrulnyko ........... A61M 29/00 604/28 |
| 2018/0117237 | A1 | 5/2018 | Brugger et al. |
| 2020/0147287 | A1* | 5/2020 | Donato ................ B01D 71/76 |

FOREIGN PATENT DOCUMENTS

| | | |
|---|---|---|
| JP | 6145772 A | 3/1986 |
| WO | 9220383 A1 | 11/1992 |
| WO | 2017001357 | 1/2017 |
| WO | 2021/119195 A1 | 6/2021 |
| WO | 2021/119197 A1 | 6/2021 |

OTHER PUBLICATIONS

International Application No. PCT/US2020/064110, International Search Report and Written Opinion mailed on Apr. 13, 2021, 13 pages.

Application No. PCT/US2020/064112, International Search Report and Written Opinion, Mailed on Mar. 10, 2021, 15 pages.

EP Application No. EP20898090.4, Extended European Search Report, Dec. 8, 2023, 7 pages.

U.S. Appl. No. 17/743,167, Non-Final Office Action, Oct. 10, 2024, 10 pages.

JP Application No. 2022-535621, Office Action, Sep. 3, 2024, 8 pages.

* cited by examiner

EXTRACORPOREAL BLOOD TREATMENT SYSTEMS AND METHODS EMPLOYING BATCH PROCESSING

CROSS-REFERENCES TO RELATED APPLICATIONS

This application is a Continuation-in-Part (CIP) application of PCT/US2020/064110, filed Dec. 9, 2020, which application claims priority to US Provisional Patent Application Nos. 62/947,312, filed Dec. 12, 2019, 63/057,129, filed Jul. 27, 2020, and the CIP application also claims priority to 63/164,202, filed Mar. 22, 2021, the teachings all of which are hereby incorporated by reference in their entireties for all purposes.

FIELD OF THE INVENTION

The present disclosure relates generally to extracorporeal blood treatments, and more particularly, to extracorporeal blood treatment systems and methods employing batch processing.

BACKGROUND OF THE INVENTION

In extracorporeal blood treatments, blood from a patient (e.g., human or animal) is withdrawn for treatment processing, and the processed blood is subsequently returned to the patient. Conventional extracorporeal blood treatment methods include but are not limited to apheresis, plasmapheresis, hemoperfusion (HPF), and renal replacement therapies (RRT), such as hemodialysis (HD), hemofiltration (HF), and hemodiafiltration (HDF). Blood-based RRT systems generally require access to the patient's vascular stream. In conventional RRT systems, sufficient clearance of waste molecules and/or fluids from the processed blood requires a certain blood flow rate through the treatment module.

To accommodate the required blood flow rate for treatment, conventional RRT systems typically require a pair of lumens or needles connected to the patient's blood stream. One of the lumens/needles pulls blood from the patient while the other lumen/needle returns processed blood to the patient, thereby enabling the minimum blood flow required for adequate treatment. For example, conventional RRT systems employ a dual-lumen catheter with a diameter of 11-13 French, an arterio-venous graft, or a matured arterio-venous fistula, all of which require maintenance to assure patency and may be associated with potential complications. Higher clearance levels may require even higher blood flow rates, thereby necessitating larger bores for the lumens/needles withdrawing blood from and returning blood to the patient.

Embodiments of the disclosed subject matter may address one or more of the above-noted problems and disadvantages, among other things, as well as offering other advantages.

BRIEF SUMMARY OF THE INVENTION

Embodiments of the disclosed subject matter provide extracorporeal blood treatment systems and methods that decouple the blood flow during treatment processing from the blood flow to/from the patient. As a result, higher blood flow rates during the treatment processing can be obtained for improved solute clearance, including increased clearance of middle molecules over conventional systems. Since the treatment processing is decoupled from the blood withdrawal and infusion, a lower blood flow rate can be used for withdrawal/infusion of blood, thereby enabling a smaller bore/diameter for the needle or lumen providing access to the patient's vascular system. Although the present disclosure uses "blood" as an exemplary body fluid, those of skill in the art will recognize that the systems and methods of the present disclosure are also useful for other body fluids such as blood, lymph, ascites, abdominal fluid, pleural fluid, organ fluid, spinal fluid, intestinal fluid or water. Similarly, although "vascular access" is an exemplary embodiment, a skilled artisan will recognize that abdominal access is needed for ascites, spinal canal access is needed for spinal fluid, and lymphatic access is need for lymph.

In embodiments, the decoupling can be achieved by batch processing of blood. For example, a volume of blood is removed from the patient to a batch container. Blood in the batch container is subsequently processed by a treatment module, before being returned to the patient. The use of batch processing allows a single conduit or lumen to be used for both withdrawal of blood from the patient and later infusion of processed blood to the patient, unlike conventional RRT systems where two lumens are used to simultaneously withdraw blood from and infuse processed blood to the patient. In some embodiments, processed blood can be returned to the batch container and repeatedly processed by the treatment module (e.g., passing through the treatment module multiple times) to further improve solute clearance.

In some embodiments, a technique according to the disclosed subject matter may be considered a single-lumen alternating micro-batch (SLAMB) technique, which utilizes a small single lumen (e.g., smaller than either 7 French, such as 6, 5, 4, or 3 French or 17 gauge such as 16, 15, 14, 13, 12, 11, or 10 gauge) to draw, at a first flow rate, a "micro" batch of blood or body fluid (e.g., about 10-300 ml, or 2-7% such as about 2, 3, 4, 5, 6, or 7% of the patient's total blood volume) into a single reservoir. The volume of body fluid can be, for example, about 10 ml-100 ml, 10 ml to 200 ml, 10 ml to 300 ml, 10 ml to 400 ml, 10 ml to 500 ml, 10 ml to 600 ml, 10 ml to 700 ml, 10 ml to 800 ml, 10 ml to 900 ml or 10 ml-1000 ml. Once in the reservoir, the batch of blood can be circulated at a higher second flow rate through a treatment module, such as hemofilter, hemodialyzer, or hemoperfusion device, thereby enabling efficient small and middle molecule clearance. After sufficient circulations, the blood is returned, at third flow rate (which may be the same as or different from the first flow rate) to the patient via the small single lumen. The cycle can then be repeated multiple times, for example, to process an entire blood volume of the patient.

In one or more embodiments, a body fluid treatment method can comprise conveying a volume of body fluid via a first conduit from an access of a patient to a chamber at a first flow rate, the first conduit having only a single lumen. The method can further comprise conveying the body fluid from the chamber through a filtration device at a second flow rate to perform an extracorporeal treatment on the body fluid and returning the treated body fluid to the chamber. The method can also comprise returning the body fluid from the chamber to the access of the patient at a third flow rate via the first conduit. The second flow rate can be decoupled from both the first and third flow rates.

More specifically, when blood is the body fluid, in one or more embodiments, a blood treatment method can comprise conveying a volume of blood via a first conduit from a vascular access of a patient to a blood chamber at a first flow rate, the first conduit having only a single lumen. The method can further comprise conveying the blood from the blood chamber through a filtration device at a second flow rate to perform an extracorporeal treatment on the blood and returning the treated blood to the blood chamber. The method can also comprise returning the blood from the blood chamber to the vascular access of the patient at a third flow rate via the first conduit. The second flow rate can be decoupled from both the first and third flow rates.

In one or more embodiments, a body fluid treatment system can comprise a processing fluid circuit, an interfacing circuit, and a controller. The processing fluid circuit can have a reservoir, a first pump, and a filtration device. An inlet of the reservoir can be coupled to an outlet of the filtration device, and an outlet of the reservoir can be coupled to an inlet of the filtration device such that body fluid from the reservoir is recirculated through the filtration device in a first direction via the first pump. The interfacing circuit can have a first conduit and a second pump. The first conduit can be coupled to the reservoir and has only a single lumen. The second pump is switchable between a first operation mode where a batch of body fluid is conveyed from an access of a patient via the first conduit and a second operation mode where body fluid from the reservoir is conveyed to the access via the first conduit for infusion into the patient. The controller can be configured to control operation of the first and second pumps in performing an extracorporeal treatment on the batch of body fluid from the patient.

More specifically, when blood is the body fluid, in one or more embodiments, a blood treatment system can comprise a processing fluid circuit, an interfacing circuit, and a controller. The processing fluid circuit can have a reservoir, a first blood pump, and a filtration device. An inlet of the reservoir can be coupled to a blood outlet of the filtration device, and an outlet of the reservoir can be coupled to a blood inlet of the filtration device such that blood from the reservoir is recirculated through the filtration device in a first direction via the first blood pump. The interfacing circuit can have a first conduit and a second blood pump. The first conduit can be coupled to the reservoir and has only a single lumen. The second blood pump is switchable between a first operation mode where a batch of blood is conveyed from a vascular access of a patient via the first conduit and a second operation mode where blood from the reservoir is conveyed to the vascular access via the first conduit for infusion into the patient. The controller can be configured to control operation of the first and second blood pumps in performing an extracorporeal treatment on the batch of blood from the patient.

In one or more embodiments, a body fluid treatment system can comprise a reservoir, a first conduit, a filter, a recirculating processing loop, a first pump, and a controller. The reservoir can hold a batch of body fluid from a patient. The first conduit can convey body fluid from an access of the patient during a first stage and can return treated body fluid to the access during a third stage. The first conduit has only a single lumen. The filter can perform an extracorporeal treatment on body fluids passing therethrough by removing waste molecules and/or fluid, thereby allowing ultrafiltration. The recirculating processing loop can connect the reservoir to the filter. Although a processing loop can connect the reservoir to the filter, this process can also be performed using a Harvard apparatus or syringe pump. The first blood pump or Harvard apparatus can convey blood in the recirculating processing loop. The controller can control the first pump to repeatedly circulate body fluid from the reservoir through the filter during a second stage between the first and third stages.

More specifically, when blood is the body fluid, in one or more embodiments, a blood treatment system can comprise a reservoir, a first conduit, a filter, a recirculating blood processing loop, a first blood pump, and a controller. The reservoir can hold a batch of blood from a patient. The first conduit can convey blood from a vascular access of the patient during a first stage and can return treated blood to the vascular access during a third stage. The first conduit has only a single lumen. The filter can perform an extracorporeal treatment on blood or body fluids passing therethrough by removing waste molecules and/or fluid, thereby allowing ultrafiltration. The recirculating blood processing loop can connect the reservoir to the filter. Although a processing loop can connect the reservoir to the filter, this process can also be performed using a Harvard apparatus or syringe pump. The first blood pump or Harvard apparatus can convey blood in the recirculating processing loop. The controller can control the first blood pump to repeatedly circulate blood from the reservoir through the filter during a second stage between the first and third stages.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described with reference to the accompanying drawings, which have not necessarily been drawn to scale. Where applicable, some elements may be simplified or otherwise not illustrated in order to assist in the illustration and description of underlying features. Throughout the figures, like reference numerals denote like elements.

DETAILED DESCRIPTION OF THE INVENTION

Extracorporeal blood treatment systems and methods according to the present disclosure employ batch processing of blood to allow decoupling of the blood flow rate during treatment processing from the blood flow rates used to withdraw/infuse blood from/to the vascular system of a patient (e.g., human or animal). The decoupling of blood flow rates allows for higher blood flow rates during treatment processing to achieve improved clearance, while also allowing for lower blood flow rates to/from the patient, thereby reducing access size (e.g., needle or catheter size) and/or number (e.g. withdraw and infusion ports or access).

Figure 1A:
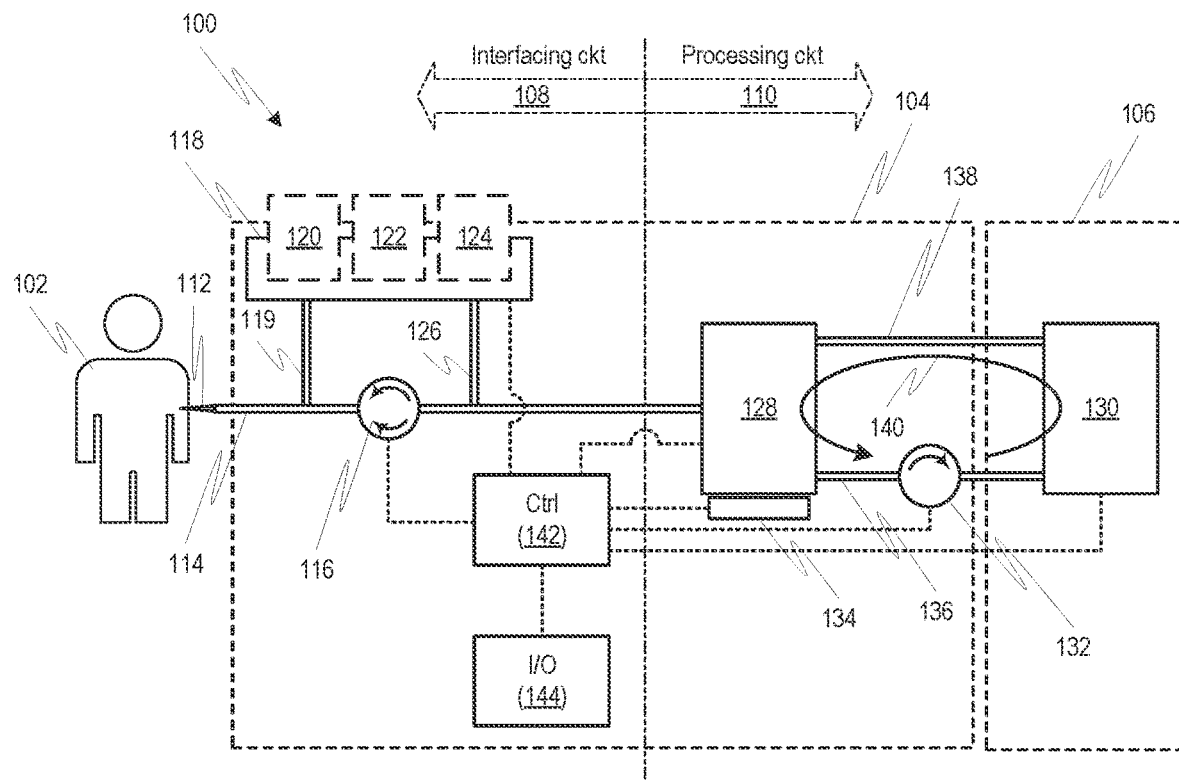
FIG. 1A is a simplified schematic diagram of a generalized blood treatment system employing batch processing, according to one or more embodiments of the disclosed subject matter.

FIG. 1A illustrates aspects of a generalized blood treatment system 100 that employs batch processing. The system 100 can include a primary module 104 and a treatment module 106. The primary module 104 can be designed to transfer blood to/from patient 102 and hold blood for processing. For example, a vascular access 112 is coupled to a single-lumen I/O conduit 114 to provide blood from patient 102 to primary module 104 for processing. The vascular access 112 can comprise a needle, catheter, or any other device for connecting to the patient vascular system known in the art. The treatment module 106 can be designed to affect a treatment on blood passing thereto, for example, a dialysis treatment including, but not limited to, hemofiltration (HF), hemodiafiltration (HDF), hemodialysis (HD), or hemoperfusion (HPF).

In some embodiments, modules 104, 106 may be constructed as separate components and connected to each other by appropriate blood-compatible connectors. For example, the primary module 104 may be a standalone system with releasable connectors that allow an installed treatment module 106 performing one type of blood treatment to be swapped out or switched for another treatment module performing another type of blood treatment. Alternatively or additionally, the swapping of treatment modules 106 installed in primary module 104 may be effective to renew or enhance a treatment component (e.g., an HPF device) expended in the blood processing. Thus, the system 100 may offer different blood or body fluid treatments by simply replacing the treatment module 106 installed to the primary module 104.

In some embodiments, system 100 may be considered to have an interfacing circuit 108 that conveys blood to/from patient 102 and a processing circuit 110 that treats the blood. For example, the interfacing circuit 108 may be constituted by components fully or substantially contained in primary module 104, while the processing circuit 110 may be constituted by some components contained in primary module 104 and other components contained in treatment module 106. The interfacing circuit 108 can include, for example, single lumen I/O conduit 114, a first blood pump 116, and a fluid/drug module 118 with associated supply conduits 119, 126. The first pump 116 can be a Harvard apparatus or syringe pump or infuse/withdraw pump. The processing circuit 110 can include, for example, a blood reservoir or chamber 128, a second blood pump 132, a treatment device 130 (e.g., filtration device), and conduits 136, 138 that form a recirculation fluid circuit 140 between the reservoir 128 and treatment device 130. The second pump 132 can be a Harvard apparatus or syringe pump or infuse/withdraw pump.

In some embodiments, system 100 may also include a controller 142 operatively coupled to the various components of the interfacing 108 and processing 110 circuits for controlling operation thereof to effect batch processing and blood treatment. System 100 may also include an input/output (I/O) module 144, which can be operatively coupled to the controller 142. In some embodiments, the I/O module 144 can be configured to convey control signals, data, or any other information to external systems, for example, to coordinate operation of system 100 with other treatment devices (e.g., as described below with respect to FIG. 3) or to convey a status of treatment to a local or remote monitoring system. Alternatively or additionally, the I/O module 144 can receive operating instructions from and/or provide information (e.g., visual or auditory) to a medical operator of the system 100 or the patient 102.

Figure 2A:
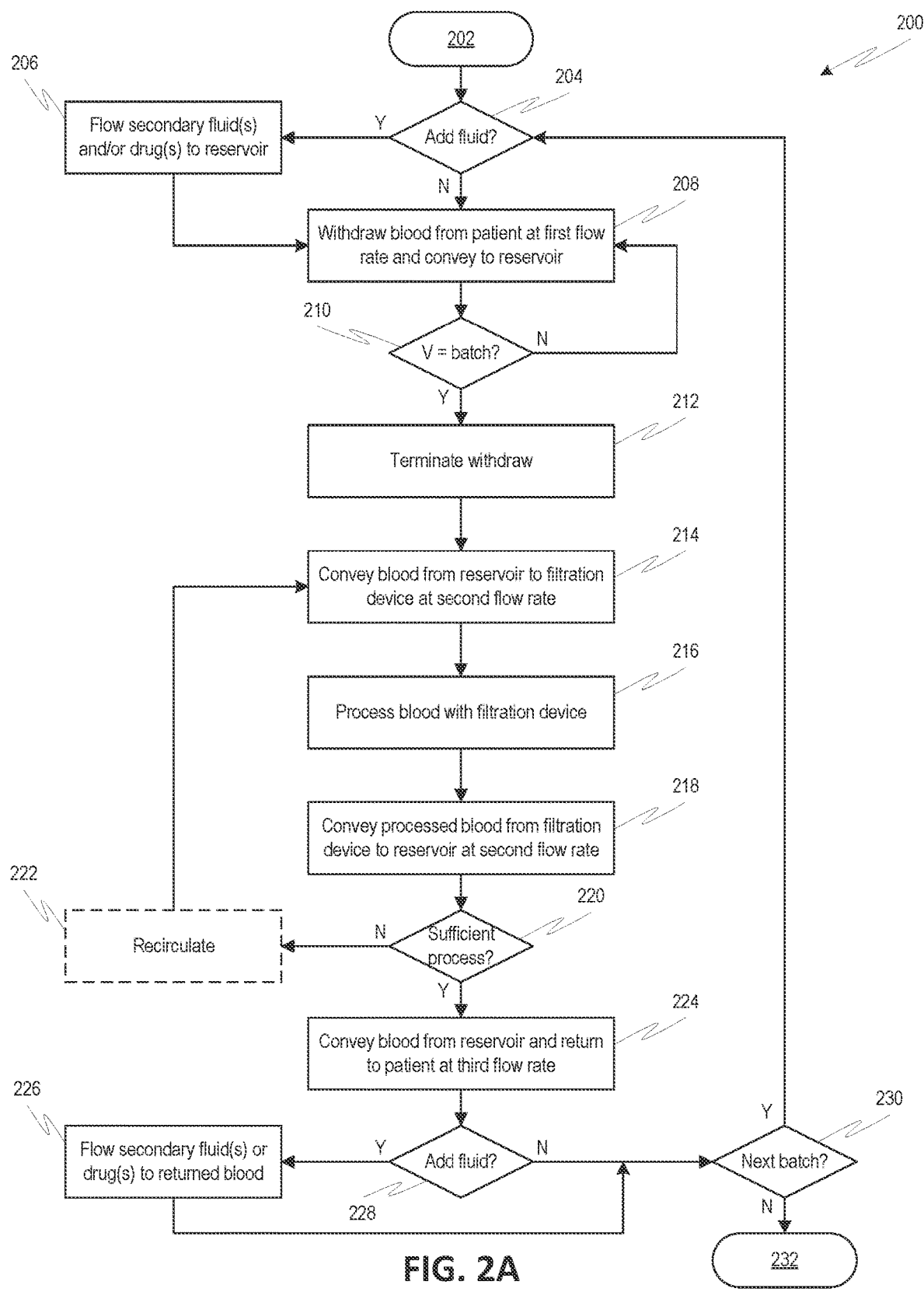
FIG. 2A is a process flow diagram for a generalized blood treatment method employing batch processing, according to one or more embodiments of the disclosed subject matter.

Referring to FIGS. 1A and 2A, an exemplary process 200 for operation of system 100 will be described. The process 200 can initiate at 202 and proceed to 204, where it is determined if a secondary fluid or drug is to be added to the blood reservoir 128. For example, controller 142 can determine if secondary fluid addition is required based on the type of treatment module 106, the type of blood treatment to be performed, and/or custom instructions received via I/O 144. For example, when treatment module 106 provides HDF, controller 142 can instruct the addition of hemofiltration or replacement fluid. Alternatively or additionally, the controller 142 can instruct the addition of a drug or a therapeutic agent. For example, when the patient has not otherwise been dosed with an anticoagulant, controller 142 can instruct the addition of an appropriate anticoagulant, such as, but not limited to heparin, citrate-based anticoagulants, nafamostat, or epoprostenol.

If it is determined at 204 that secondary fluid and/or drug is to be added, the process 200 can proceed to 206, where the secondary fluid and/or drug is flowed from secondary fluid supply 120 and/or anticoagulant supply 122 in fluid/drug module 118 to the blood reservoir 128. For example, controller 142 can control fluid/drug module 118, first pump 116, and various valves or other fluid control components (not shown) to pump secondary fluid and/or anticoagulant from module 118 via one or more input conduits 119 to single-lumen conduit 114, and then on to blood reservoir 128.

Once sufficient secondary fluid and/or drug has been provided to reservoir 128, or when it is otherwise determined at 204 that secondary fluid or drugs are not needed, the process 200 can proceed to 208, where blood is withdrawn from patient 102 via access 112 and conveyed to reservoir 128 for temporary storage until treatment processing. For example, controller 142 can control first pump 116 and various valves or other fluid control components (not shown) to pump the blood from patient 102 along single-lumen conduit 114 to the reservoir 128 at a first flow rate. The blood conveying 208 can continue via 210 until a predetermined blood volume (V) is obtained in the reservoir 128. The predetermined blood volume may be adjustable based on a size of patient 102, for example, 2-7% or 1-15% such as 1, 2, 3, 4, 5, 6, 7, 8, 9, 10, 11, 12, 13, 14 or 15% of a total blood volume of patient 102. For example, the predetermined blood volume may be 10-300 ml, or 10 ml to 1000 ml and may be set by the patient 102 or system operator via I/O module 144.

The controller 142 can monitor the volume of blood in reservoir 128 and determine at 210 whether the predetermined blood volume has been met. For example, a weight of reservoir 128 and contents therein can be monitored by a highly-accurate weight sensor 134, e.g., a gravity scale. Because the blood volume in reservoir 128 is relatively small (e.g., less than 300 ml), the reservoir 128 should be weighed very accurately to avoid incorrect volume correlations. For example, the weight sensor may have an accuracy down to 1 gram or less. Those of skill in the art will know of other sensors to measure fluid level including, but not limited to, floats, gauges, capacitive level sensors, light sensors and other volume or weight sensors, which can be used.

Controller 142 can then correlate changes in weight of reservoir 128 to changes in fluid/blood volume therein. Controller 142 can also correlate changes or the presence of a signal when other volume levels sensors are used. In some embodiments, weight sensor 134 provides signals to controller 142 in real-time during fill of reservoir 128. The sensor 134 and/or controller 142 may thus be configured to compensate for any weight fluctuations due to fluid dynamics/vibration within the reservoir during the blood flow 208. Alternatively or additionally, controller 142 may sample signals from the weight sensor 134 and determine at 210 if sufficient volume has been achieved during intermittent pauses in flow 208 to allow blood in reservoir 128 to settle.

Although 208-210 is shown as occurring after 204-206, it is also possible in some embodiments that the order may be reversed, i.e., such that blood is withdrawn from patient 102 and stored in reservoir 128 before the addition of secondary fluid and/or anticoagulant to the reservoir 128. Moreover, in some embodiments, fluid conveyances other than pump 116 can be used for the secondary fluid or anticoagulant. For example, input conduit 119 of fluid/drug module 118 may bypass single-lumen conduit 114 and interface directly with the blood reservoir 128. A fluid conveyance (not shown) arranged between the fluid/drug module 118 and the reservoir 128 can transport the secondary fluid or anticoagulant to reservoir 128, such that secondary fluid/drug flow 206 may be able to occur simultaneously with supply 208 of blood to the reservoir 128. The fluid conveyance may be a fluid pump similar to pump 116, a Harvard apparatus, a syringe pump, a gravity-feed controlled by an appropriate valve, or any other device known in the art.

Once the predetermined blood volume in reservoir 128 has been reached at 210, the process 200 can proceed to 212, where withdrawal of blood from patient 102 is terminated. For example, controller 142 can control first pump 116 and various valves or other fluid control components (not shown) to stop the blood flow from patient 102 and to otherwise isolate single-lumen conduit 114 from blood reservoir 128 for subsequent treatment processing.

The process 200 can thus proceed to 214, where blood treatment processing may initiate. In particular, blood from reservoir 128 (potentially with secondary fluid and/or anticoagulant) is conveyed at 214 to filtration device 130, where the blood is subjected to a treatment process at 216 (e.g., flowing through to effect a dialysis treatment), and then returned to the reservoir 128 at 218. For example, controller 142 can control second pump 132 and various valves or other fluid control components (not shown) to flow blood from reservoir 128 along conduit 136, through filtration device 130, and back to reservoir 128 via conduit 138. The flowing of blood in each of 214-218 may be at a second flow rate. In general, the second flow rate is greater than the first flow rate (used to withdraw blood from patient 102) to enhance solute clearance efficiency. For example, the second flow rate can be 50-500 ml/min and may be at least 1.25 times, and preferably at least 2 times, greater than the first flow rate.

In other words, the first and or third flow rate is about 5 ml/min to about 250 ml/min, or about 5 ml/min, 10 ml/min, 15 ml/min, 20 ml/min, 25 ml/min, 30 ml/min, 35 ml/min, 40 ml/min, 45 ml/min, 50 ml/min, 55 ml/min, 60 ml/min, 65 ml/min, 70 ml/min, 75 ml/min, 80 ml/min, 85 ml/min, 90 ml/min, 95 ml/min, 100 ml/min, 105 ml/min, 110 ml/min, 115 ml/min, 120 ml/min, 125 ml/min, 130 ml/min, 135 ml/min, 140 ml/min, 145 ml/min, 150 ml/min, 155 ml/min, 160 ml/min, 165 ml/min, 170 ml/min, 175 ml/min, 180 ml/min, 185 ml/min, 190 ml/min, 195 ml/min, 200 ml/min, 205 ml/min, 210 ml/min, 215 ml/min, 220 ml/min, 225 ml/min, 230 ml/min, 235 ml/min, 240 ml/min, 245 ml/min, and/or 250 ml/min.

The second flow rate is at least 1.25 times, and preferably at least 2 times, greater than the first flow rate or 50-750 ml/min, or about 50 ml/min, 55 ml/min, 60 ml/min, 65 ml/min, 70 ml/min, 75 ml/min, 80 ml/min, 85 ml/min, 90 ml/min, 95 ml/min, 100 ml/min, 105 ml/min, 110 ml/min, 115 ml/min, 120 ml/min, 125 ml/min, 130 ml/min, 135 ml/min, 140 ml/min, 145 ml/min, 150 ml/min, 155 ml/min, 160 ml/min, 165 ml/min, 170 ml/min, 175 ml/min, 180 ml/min, 185 ml/min, 190 ml/min, 195 ml/min, 200 ml/min, 205 ml/min, 210 ml/min, 215 ml/min, 220 ml/min, 225 ml/min, 230 ml/min, 235 ml/min, 240 ml/min, 245 ml/min, 250 ml/min, 255 ml/min, 260 ml/min, 265 ml/min, 270 ml/min, 275 ml/min, 280 ml/min, 285 ml/min, 290 ml/min, 295 ml/min, 300 ml/min, 305 ml/min, 310 ml/min, 315 ml/min, 320 ml/min, 325 ml/min, 330 ml/min, 335 ml/min, 340 ml/min, 345 ml/min, 350 ml/min, 355 ml/min, 360 ml/min, 365 ml/min, 370 ml/min, 375 ml/min, 380 ml/min, 385 ml/min, 390 ml/min, 395 ml/min, 400 ml/min, 405 ml/min, 410 ml/min, 415 ml/min, 420 ml/min, 425 ml/min, 430 ml/min, 435 ml/min, 440 ml/min, 445 ml/min, 450 ml/min, 455 ml/min, 460 ml/min, 465 ml/min, 470 ml/min, 475 ml/min, 480 ml/min, 485 ml/min, 490 ml/min, 495 ml/min, 500 ml/min, 505 ml/min, 510 ml/min, 515 ml/min, 520 ml/min, 525 ml/min, 530 ml/min, 535 ml/min, 540 ml/min, 545 ml/min, 550 ml/min, 555 ml/min, 560 ml/min, 565 ml/min, 570 ml/min, 575 ml/min, 580 ml/min, 585 ml/min, 590 ml/min, 595 ml/min, 600 ml/min, 605 ml/min, 610 ml/min, 615 ml/min, 620 ml/min, 625 ml/min, 630 ml/min, 635 ml/min, 640 ml/min, 645 ml/min, 650 ml/min, 655 ml/min, 660 ml/min, 665 ml/min, 670 ml/min, 675 ml/min, 680 ml/min, 685 ml/min, 690 ml/min, 695 ml/min, 700 ml/min, 705 ml/min, 710 ml/min, 715 ml/min, 720 ml/min, 725 ml/min, 730 ml/min, 735 ml/min, 740 ml/min, 745 ml/min, and/or 750 ml/min.

At 220, it can be determined if the blood in reservoir 128 has been subjected to sufficient treatment processing by 214-218. For example, controller 142 can determine whether sufficient treatment has occurred based on an elapsed time of the processing, a magnitude of the second flow rate, and/or a volume of the blood batch in reservoir 128. If sufficient processing has not been achieved at 220, the process 200 can proceed to 222, where the blood is optionally recirculated and reprocessed by returning to 214. Thus, in embodiments, the flowing of blood along recirculation circuit 140 in 214-218 can be repeated such that each portion of the blood passes through filtration device 130 more than twice (e.g., 2-10 times), and preferably several times in an iterative process. For example, the recirculation of blood may be such that the entire volume of the reservoir passes through the filtration device at least three times before being returned to the patient. The repeated processing of the same blood by the filtration device may achieve further improved clearance efficiency as compared to conventional single-pass RRT systems.

Alternatively or additionally, controller 142 can correlate changes in weight of reservoir 128 (or other fluid level sensor as measured by sensor 134) to a stage of treatment processing. For example, an amount of fluid removed from the blood by the filtration device 130 can correlate with a stage of the treatment, which fluid removal can be detected in changes in instantaneous or average weight or level of fluid of reservoir 128 and contents therein. Thus, in some embodiments, weight sensor 134 provides signals to controller 142 in real-time during flow of blood from/to reservoir 128. The sensor 134 and/or controller 142 may thus be configured to compensate for any weight fluctuations due to fluid dynamics/agitation within the reservoir during the blood flows 214-218. Alternatively or additionally, controller 142 may sample signals from the weight sensor 134 and determine at 220 if sufficient processing has been achieved during intermittent pauses in blood flows 214-218 to allow blood in reservoir 128 to settle.

Although shown as separate sequential steps in FIG. 2A, in practice 214-222 may occur simultaneously, with blood recirculating between reservoir 128 and filtration device 130 continuously until sufficient processing has been achieved at 220. In some embodiments, the continuous recirculation may be periodically interrupted, for example, to allow for a more accurate weight measurement or fluid volume level of blood or body fluid reservoir 128 by sensor 134.

Once sufficient treatment processing of blood in reservoir 128 has been reached at 220, the process can proceed to 224, where the recirculation 222 is terminated and treated blood in reservoir 128 is returned to patient 102 via access 112. For example, controller 142 can control first pump 116 and various valves or other fluid control components (not shown) to pump the blood from reservoir along single-lumen conduit 114 to the access 112 at a third flow rate. Since the blood return uses the same conduit 114 and access 112 as the blood withdrawal, the third flow rate can be, but does not need to be, the same as the first flow rate.

The process 200 can then proceed to 228, where it is determined if a secondary fluid or drug is to be added to patient 102. For example, when the patient was previously dosed with anticoagulant at 206, controller 142 can instruct the addition of an appropriate anticoagulant reversal agent, such as, but not limited to protamine and/or calcium. Alternatively or additionally, controller 142 can determine if secondary fluid addition to patient 102 is required based on the type of treatment module 106, the type of blood treatment performed, and/or custom instructions received via I/O 144. For example, controller 142 can instruct the infusion of a volume of replacement fluid such as albumin to patient 102. Alternatively or additionally, the controller 142 can determine at 228 to use secondary fluid (e.g., buffer or saline) from module 118 to flush conduit 114 and access 112 in preparation for a subsequent batch at 230.

If it is determined at 228 that secondary fluid and/or drug is to be added, the process 200 can proceed to 226, where the secondary fluid and/or drug is flowed from secondary fluid supply 120 and/or anticoagulant reversal supply 124 in fluid/drug module 118 to the patient 102.

For example, controller 142 can control fluid/drug module 118, first pump 116, and various valves or other fluid control components (not shown) to pump secondary fluid and/or anticoagulant reversal agent from module 118 via one or more input conduits 126 to single-lumen conduit 114, and then on to patient 102.

Once sufficient secondary fluid and/or drug has been provided to patient 102, or when it is otherwise determined at 228 that secondary fluid or drugs are not needed, the process 200 can proceed to 230, where it is determined if another batch of blood for the same patient 102 should be processed. For example, controller 142 can control system 100 to repeat process 200 for multiple sequential batches until an entire blood volume of the patient 102 has been processed (e.g., 4-6 liters of blood). Alternatively or additionally, controller 142 can control system 100 to repeat process 200 until a predetermined time limit or predetermined number of repetitions or volume of body fluid has been reached. I/O module 144 can be used by the patient 102 or operator to set the predetermined time limit or number of repetitions or volume of body fluid. If further batches are desired at 230, the process 200 returns to 204. Otherwise, the process 200 may terminate at 232 until initiated again for the same patient 102 or a different patient.

In one embodiment, the present disclosure provides a blood treatment method comprising:
 (a) conveying a volume of blood via a first conduit from a vascular access of a patient to a blood chamber at a first flow rate, the first conduit having only a single lumen;
 (b) conveying the blood from the blood chamber through a filtration device, plasma separator, hemoadsorption device, and/or oxygenator/carbon dioxide removal device at a second flow rate to perform an extracorporeal treatment on the blood and returning the treated blood to the blood chamber;
 (c) waiting a period of time before returning a portion of the blood in the reservoir back to the patient; and
 (d) returning the blood from the blood chamber to the vascular access of the patient at a third flow rate via the first conduit, wherein the second flow rate is decoupled from both the first and third flow rates.

In certain instances, the first flow rate is between 25-1,000 mL/min.

In certain instances, the third flow rate is between 25-1,000 mL/min.

In certain instances, the period of time in step (b) is between 0 and 200 seconds.

In certain instances, steps (a) to (d) are repeated for continuous flow.

In certain instances, steps (a), (c) and (d) occur, while step (b) occurs in simultaneous fashion.

In certain instances, the period of time in step (c) is sufficient to fill the reservoir to a threshold level.

In certain instances, the steps (a), (c) and (d) occur continuously in a fill-return tidal manner.

In certain other embodiments, system 100 of FIG. 1A can be used to treat a body fluid (e.g. blood) in tidal mode processing as an alternative to batch processing. In tidal mode, blood is removed from patient 102 and placed in reservoir 128 in continuous fill and empty fashion. In parallel, blood flows through recirculation circuit 140 between reservoir 128 and treatment device 130. In other words, the interfacing circuit 108, which is infusing and withdrawing pump blood is filling the reservoir 128 and emptying the reservoir 128 continuously, while the processing circuit 110 is continuously recirculating blood between the reservoir 128 and treatment device 130.

In certain aspects, the first pump 116 withdraws blood from patient 102 and fills reservoir 128 continuously, while second pump 132 continuously conveys blood from reservoir 128 to treatment device 130 through recirculation circuit 140. This continuous movement of blood through both the interfacing circuit 108 and the processing circuit 110 aids in preventing blood clots.

In tidal mode processing, once a predetermined amount of blood volume in reservoir 128 is reached, the blood volume toggles back to patient 102. Simultaneously, blood from reservoir 128 (potentially with secondary fluid and/or anticoagulant) is conveyed to filtration device 130, where the blood is subjected to a treatment process (e.g., flowing through to effect a dialysis treatment), and then returned to the reservoir 128. Both processes are occurring continuously and simultaneously. In general, the second flow rate (treatment processing) is greater than the first flow rate (used to withdraw blood from patient 102 to enhance solute clearance efficiency and prevent coagulation of blood). For example, the second flow rate can be 50-500 ml/min and may be at least 1.25 times, and preferably at least 2 times, greater than the first flow rate.

Like batch processing, in tidal mode processing the treatment processing is also decoupled from the blood withdrawal and infusion processes. Thus a lower blood flow rate can be used for the withdrawal/infusion of blood, thereby enabling a smaller bore/diameter for the needle or lumen providing access to the patient's vascular system. In tidal mode processing, because the second flow rate is faster than the first and/or the third flow rate, the blood removed from patient 102 tends to be treated before being stored in reservoir 128. In certain instances, the reservoir tends to fill with treated blood and is therefore efficiently treated.

In certain instances, an anticoagulation compound is constantly flowing into the reservoir 128 such that when blood from the patient 102 comes into the reservoir 128, the blood immediately admixes with anticoagulant, so there can be immediate blood thinning. Continuous recirculation begins when the reservoir 128 is filled to a fill threshold. Recirculation here from the reservoir 128 to the filtration device 130 (e.g., hemodialyzer) continues. In tidal processing mode, the system see-saws, so the reservoir 128 contents goes back into the patient, and then it goes back to the reservoir and this continues in a back-and-forth, see-sawing from the reservoir into the patient. Simultaneously, blood from reservoir 128 is conveyed to filtration device 130, where the blood is subjected to a treatment process and then returned to the reservoir 128.

In FIG. 1A, anticoagulant supply 122 in fluid/drug module 118 can be external to system 100. In other words, an external anticoagulant pump such as in devices for mechanical circulatory support (MCS), including ventricular assist devices (VADs) or extracorporeal membrane oxygenation (ECMO) devices can be used instead of an integrated anticoagulant pump.

Figure 2B:
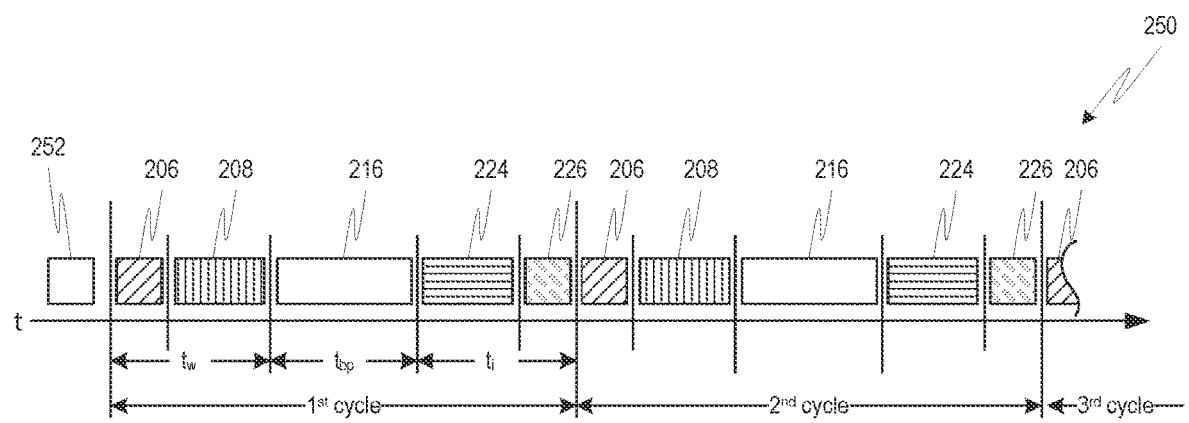
FIG. 2B is a map illustrating relative timing of various operations in a blood treatment method, according to one or more embodiments of the disclosed subject matter.

FIG. 2B shows a time map 250 corresponding to the process 200 of FIG. 2A. The overall treatment process may begin with an initial setup 252, where system 100 is connected to patient 102. For example, a needle serving as vascular access 112 can be placed into the vascular system of the patient 102 and the needle connected to single-lumen conduit 114 of system 100. Alternatively, a previously-installed catheter serving as vascular access 112 can be coupled to single-lumen conduit 114 of system 100. After appropriate setup 252, a blood batch processing cycle is performed and can be sequentially repeated on additional batches in a continuous manner or until a termination condition is met, for example, until an entire blood volume of the patient has been processed. Each blood batch processing cycle comprises a batch preparation stage (constituted by secondary fluid/drug flow 206 and blood withdrawal 208), a blood treatment stage (constituted by blood treatment 216), and a batch return stage (constituted by blood infusion 224 and secondary fluid/drug flow 226).

The batch preparation and batch return stages can employ fluid flow rates less than that of blood treatment stage. In some embodiments, the batch preparation stage and batch return stage employ fluid flow rates that are substantially the same. As such, a time ($t_w$) for the batch preparation stage and a time ($t_i$) for the batch return stage may also be substantially the same. These times may be based on a volume of the blood batch, sizes of the vascular access 112 and single-lumen conduit 114, and fluid flow rate, among other things or metrics. A time ($t_{bp}$) for the blood treatment stage may be similar to that of the other stages despite the higher fluid flow rate. Alternatively, the time ($t_{bp}$) for the blood treatment stage may be greater than that for either or both of the other stages. The blood treatment stage time ($t_{bp}$) may be based on a volume of the blood batch, type of filtration device, fluid flow rate, and desired degree of recirculation (e.g., number of passes of blood through the filtration device), among other things or metrics.

In some embodiments, the time for each cycle is designed to be less than 10 minutes. For example, the total time for each cycle may be 4-7 minutes, thereby enabling up to 15 cycles to be achieved in an hour. When using a batch volume of around 200 ml, such cycle times may achieve blood processing levels comparable to conventional RRT systems. For example, $t_{bp}$ may be around 3 minutes, with the remainder of the cycle time split equally between the remaining stages (e.g., $t_w=t_i=\sim 3.5$ minutes).

System 100 and/or process 200 (and/or any of the subsequently discussed embodiments) can be adapted to provide various dialysis treatment therapies, including continuous RRT, periodic intermittent RRT, nocturnal dialysis, daily home dialysis, or any other dialysis or blood purification application. The use of batch processing by system 100 and/or process 200 advantageously allows a single-lumen conduit 114 to be used for both withdrawal of blood from patient 102 and later infusion of processed blood to patient 102, unlike conventional RRT systems where two lumens are used to simultaneously withdraw blood from and infuse processed blood to the patient. This single access point or port can ease the burden of vascular access in both acute and chronic patients.

Moreover, the decoupling of flow rates allows for a smaller size vascular access 112 than would otherwise be required to support the second flow rate through filtration device 130. Thus, system 100 may employ needles or catheters having a size less than that typically used in conventional RRT systems, which smaller size (and reduced number) may be better tolerated (or at least less painful or intrusive) by patient 102. The decoupling of flow rates also allows a higher second flow rate to be used than would otherwise be possible with conventional RRT systems, thereby improving clearance, especially of middle molecules (e.g., 500 Daltons to 60 kD).

In general, middle-molecule clearance can be achieved using (1) a high-flux dialyzer, (2) high blood flow rates, and (3) high dialysate flow rates, the combination of which is difficult to achieve in conventional RRT systems but is readily provided by system 100. Middle-molecule clearance can be measured by a representative middle molecule such beta 2 microglobulin. For system 100 and/or process 200, middle molecule clearance as measured by beta 2 microglobulin of at least 25 ml/min, and preferably 80-130 ml/min, can be achieved. For example, system 100 and/or process 200 can achieve a middle molecule clearance as measured by beta 2 microglobulin clearance greater than 100 ml/min with a single-lumen access 114, e.g., a catheter smaller than 7 French or a needle smaller than 17 gauge.

Figure 1B:
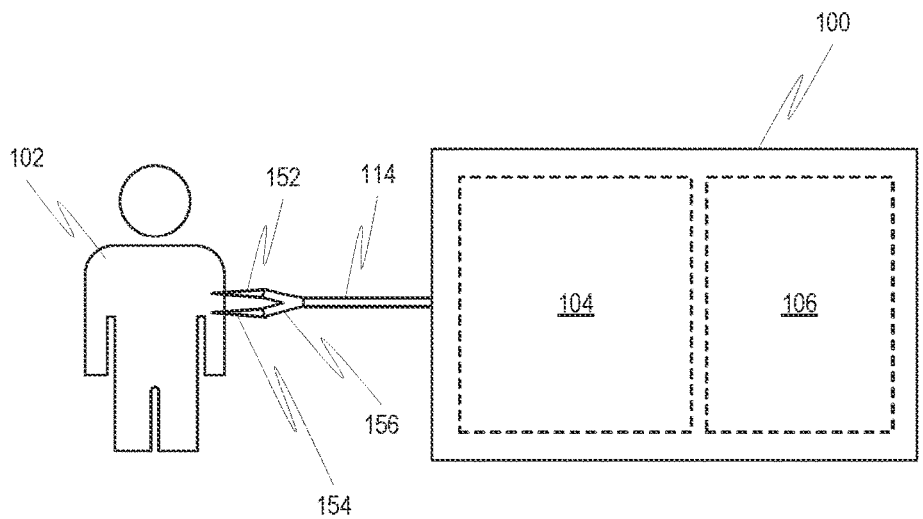
FIG. 1B is a simplified schematic diagram of the generalized blood treatment system of FIG. 1A used with a multi-line vascular access, according to one or more embodiments of the disclosed subject matter.

Although FIG. 1A shows a single vascular access 112, system 100 can also be adapted to existing setups having a two-lumen connection to the vascular system (e.g., previously-installed multi-lumen catheter or central line). For example, FIG. 1B illustrates a configuration where vascular access includes two lumens 152, 154 connected to the vascular system of patient 102. The lumens may be part of an installed multi-lumen catheter or may be separate needles inserted into the patient, e.g., at an arteriovenous fistula or graft. A fluidic union 156 (e.g., Y-connector) is provided between the patient 102 and system 100 in order to couple the separate lumens 152, 154 to the single-lumen conduit 114 of system 100. Thus, system 100 is still capable of withdrawing/infusing blood using a single-lumen (i.e., conduit 114) despite the multi-lumen vascular access.

System 100 and/or process 200 (and/or any of the subsequently discussed embodiments) may further exhibit one or more of the following advantages:

In certain aspects, blood batches can be small (e.g., ≤300 ml) and anticoagulated, and therefore a smaller capacity filtration device (e.g., hemofilter) can be utilized for the treatment processing. The smaller components may reduce system costs.

In certain aspects, the smaller filtration device coupled with relatively small batch volume can yield a footprint and/or three-dimensional size that is less than conventional RRT systems. The overall extracorporeal blood treatment system may thus be substantially portable, or at least more so than conventional RRT systems.

In certain aspects, blood batches can be small, and therefore an effective amount of anticoagulant may be used that is less than that required for conventional RRT systems.

In certain aspects, the anticoagulant may be localized (e.g., within system 100 and at the infusion site in the patient) rather than being distributed through the vascular system, which may avoid patient complications. Any anticoagulant infused into the patient may also be reversed by delivery of an anticoagulant reversal agent by the system.

In certain aspects, blood is only processed in batches, and therefore the risk of a blood leak in processing circuit 110 causing significant blood loss is mitigated. Moreover, since the first flow rate for blood withdrawal is relatively slower, the risk of significant blood loss due to a blood leak in the interfacing circuit 108 is also reduced.

In certain aspects, since the dual-lumen catheter of conventional RRT systems is not required in the disclosed systems, inefficiencies due to blood recirculation can be avoided.

In certain aspects, batch size, flow rates, and/or processing time can all be customized, for example, to take into account patient size or illness severity. Smaller withdrawal volumes of blood may decrease hemodynamic instabilities often seen when a conventional RRT session is initiated.

System 100 and/or process 200 (and/or any of the subsequently discussed embodiments) may exhibit additional or different advantages or features beyond those specifically delineated above.

In some embodiments, the methods and systems disclosed can be used to process other body fluids. For example, accumulation of fluid in the abdominal cavity is called ascites. Ascites can be common with patients with cirrhosis, liver disease or congestive heart failure. When removing a body fluid such as ascites, a diuretic can also be administered. Commonly used diuretics include spironolactone (Aldactone) and/or furosemide (Lasix). When fluid accumulation cannot be treated optimally with diuretics and a salt restricted diet, patients may require a large amount of fluid be removed (paracentesis) for relief of symptoms. The disclosure includes methods and systems for treating ascites, by the withdrawal of ascites. Optionally, the withdrawn ascitic fluid can be concentrated and reinfused.

Paracentesis is carried out under strict sterile conditions. Ascites is withdrawn from patient 102 via access 112 and conveyed to reservoir 128 for temporary storage until treatment processing. Pump 116 can be used to remove the ascitic fluid at a flow rate of from about 50 ml/min to about 200 ml/min such as about 100 ml/min to about 150 ml/min. Alternatively, ascitic fluid removal may use gravity. The needle is usually inserted into the left or right lower abdomen, where the needle is advanced through the subcutaneous tissue and then through the peritoneal cavity. In certain aspects, the ascitic fluid is drained in a single session, assisted by gentle mobilization of the cannula or turning patient 102 if necessary.

The body fluid (e.g., ascites) from reservoir 128 is conveyed to filtration device 130, where the ascites is subjected to a treatment process such as concentration and is thereafter returned to the reservoir 128. The concentrated ascites (e.g., a protein rich concentrate) can be returned to patent 102 via conduit 114. Albumin may also be infused in lieu of the concentrated ascites, or in addition to the concentrated ascites.

Figure 3:
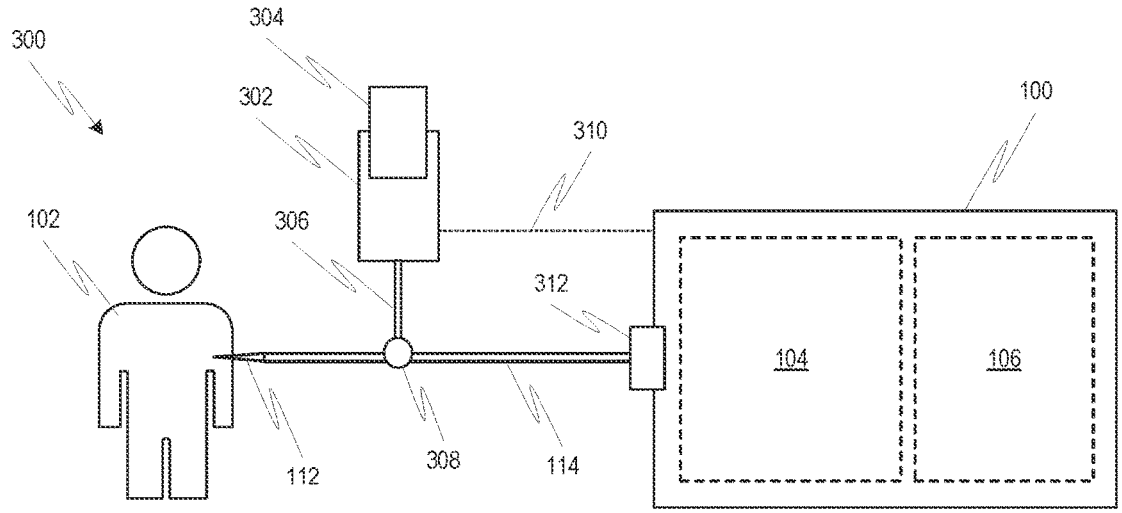
FIG. 3 is a simplified schematic diagram of a combined blood treatment and infusion system, according to one or more embodiments of the disclosed subject matter.

In some embodiments, system 100 can be combined with another medical treatment device coupled to the same vascular access. For example, FIG. 3 illustrates a system 300 that provides both fluid/drug infusion and blood treatment in a single setup. Medical treatment device 302 (e.g. infusion pump) can be connected to the blood treatment system 100 so as to share an infusion flow path to vascular access 112. For example, a fluidic coupling 308 (e.g., union connection, such as a Y-connector) can connect the single lumen conduit 114 of system 100 to an infusion supply line 306 of medical treatment device 302. In some embodiments, system 300 may be realized by providing system 100 separate from an existing infusion device 302 and operatively connecting the two together, for example, via fluidic coupling 308 and electrical signal coupling 310 (e.g., communication line). Alternatively, system 300 may be realized as a single integrated machine, where fluidic coupling 308 and electrical signal coupling 310 are internal to the machine.

In FIG. 3, the medical treatment device 302 can have a pump that infuses a fluid or drug from supply 304 into patient 102 via supply line 306, fluidic coupling 308, and vascular access 112. To coordinate operation between each other, medical treatment device 302 and system 100 may send electrical signals over electrical signal coupling 310, which may be a physical wired connection and/or a wireless connection. For example, the pump of medical treatment device 302 may pause infusion at least when blood is withdrawn from patient 102 by system 100. Medical treatment device 302 may otherwise continue infusion when blood is being processed by system 100 and/or when blood is being returned from system 100 to patient 102. In some embodiments, during infusion by medical treatment device 302 (or during at least part of the infusion), an access valve 312 can be used to cut-off system 100 from conduit 114, such that fluid/drugs from device 302 does not enter system 100. Alternatively or additionally, fluidic coupling 308 and access valve 312 may be integrated together as a single component, e.g., a fluid switch, such that only one of system 100 and medical treatment device 302 are operatively connected to vascular access 112 at a time.

Figure 4B:
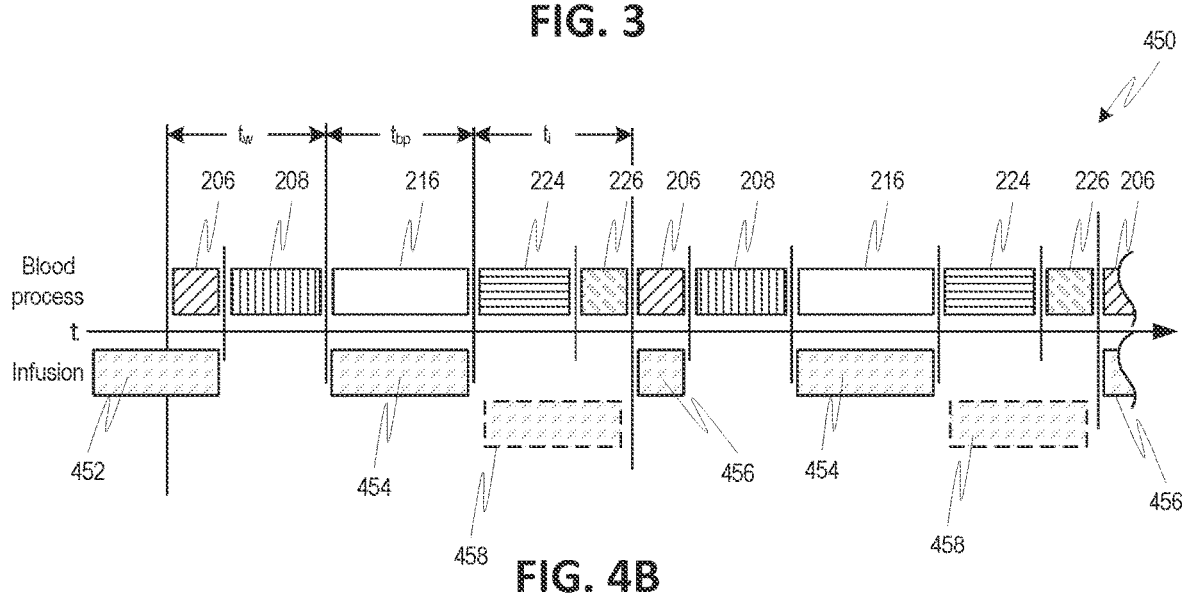
FIG. 4B is a map illustrating relative timing of various operations in a blood treatment and infusion method, according to one or more embodiments of the disclosed subject matter.
Figure 4A:
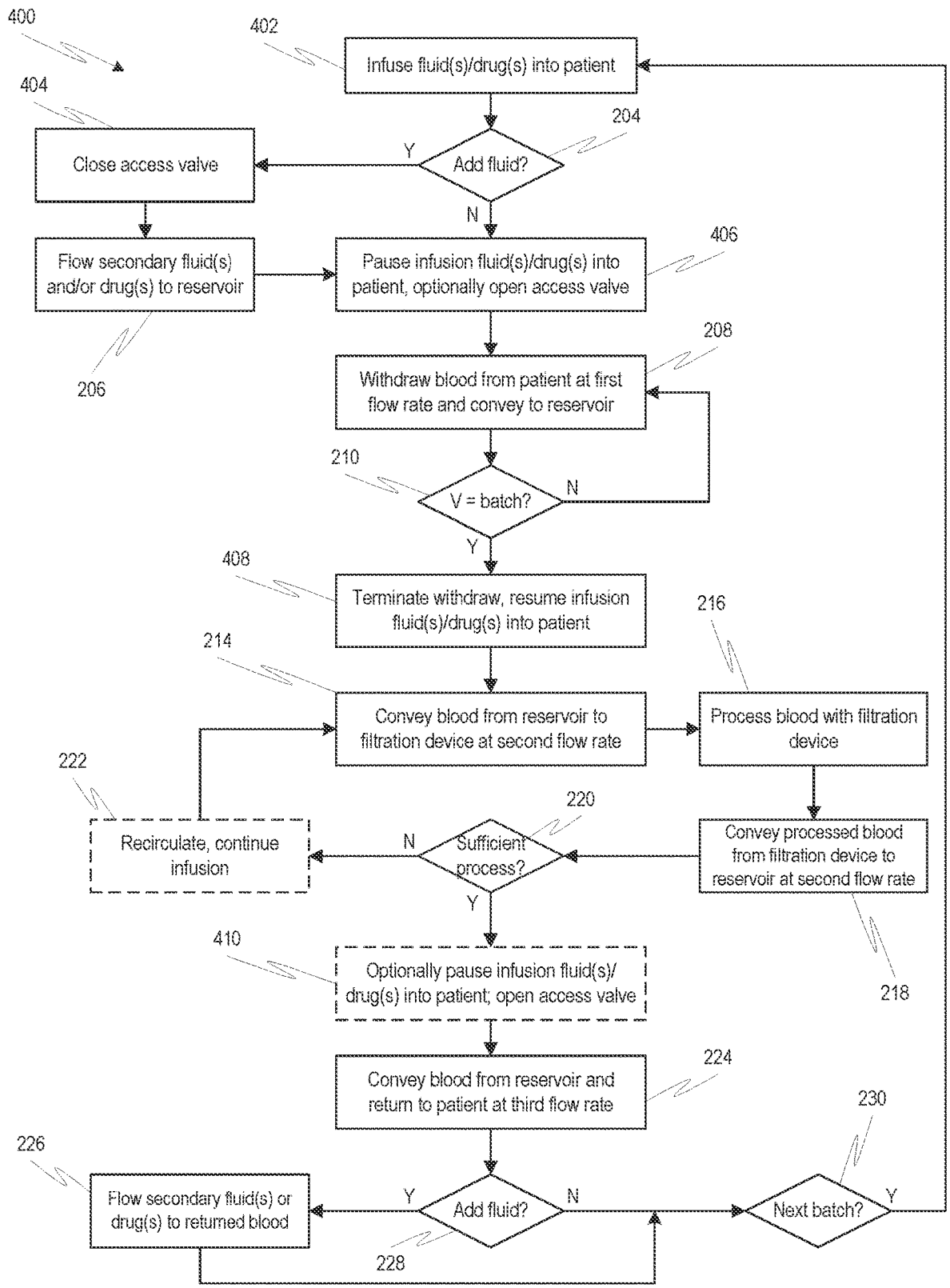
FIG. 4A is a process flow diagram for a combined blood treatment and infusion method, according to one or more embodiments of the disclosed subject matter.

Referring to FIGS. 3 and 4A, an exemplary process 400 for operation of system 300 will be described. In general, the operation of system 100 within the context of process 400 may be substantially similar to that described above with respect to process 200. Accordingly, FIG. 4A employs the same reference numbers as FIG. 2A for those operations and are not separately discussed here. Rather, the discussion below focuses on the differences of process 400 from process 200.

The process 400 can initiate at 402, where fluid or a drug from supply 304 is infused via vascular access 112 into patient 102 using medical treatment device 302. In some embodiments, the medical treatment device 302 has its own independent control system that dictates operation of infusion 402 (e.g., based on input by patient 102 or an operator). In other embodiments, the medical treatment device 302 receives instructions from controller 142 of system 100, for example, via electrical signal coupling 310.

Infusion 402 can continue until system 100 requires use of the vascular access 112 for blood withdrawal. Thus, at 204, the process 400 can determine if secondary fluid/drug should be added to reservoir 128 to begin a blood batch treatment cycle. When secondary fluid/drug is desired at 204, process 400 can optionally close access valve 312 (if not already closed) to ensure that the secondary fluid/drug only travels to reservoir 128 rather than to patient 102. Once sufficient secondary fluid and/or drug has been provided to reservoir 128, or when it is otherwise determined at 204 that secondary fluid or drugs are not needed, the process 400 can proceed to 406, where infusion by medical treatment device 302 is temporarily paused to allow blood to be withdrawn at 208 from patient 102 via access 112 and conveyed to reservoir 128. When access valve 312 has been previously closed, 406 can optionally include opening access valve 312 to allow blood to flow from vascular access 112 into system 100 via single-lumen conduit 114.

The infusion pause 406 and blood withdrawal 208 may continue until a predetermined blood volume in reservoir 128 has been achieved at 210, after which process 400 can proceed to 408, where blood withdrawal is terminated and infusion by medical treatment device 302 is resumed. The blood processing 214-218 and recirculation 222 can occur simultaneously with resumed infusion 408. Once sufficient treatment processing has been reached at 220, the process 400 can proceed in a manner similar to process 200, for example, by returning blood 224, flowing secondary fluid and/or anticoagulant reversal agent 226, and repeating at 230 for a subsequent batch. When the access valve 312 has been previously closed, 224 can optionally include opening access valve 312 to allow blood to flow from system 100 to vascular access 112 via single-lumen conduit 114. Thus, the blood return 224 by system 100 may occur simultaneously with fluid/drug infusion 408 by medical treatment device 302. In some embodiments, the blood flow rate and/or the fluid/drug infusion flow rate may be adjusted during this stage to accommodate the two simultaneous flows via the single-lumen conduit 114 and/or vascular access 112.

Alternatively, once the blood treatment processing 214-218 concludes at 220, process 400 can optionally pause infusion by medical treatment device 302 at 410, thereby allowing blood return 224 and/or secondary fluid/reversal agent flow 226 to have sole access to conduit 114 and vascular access 112. When the access valve 312 has been previously closed, 410 can optionally include opening access valve 312 to allow blood to flow from system 100 to vascular access 112 via single-lumen conduit 114.

FIG. 4B shows a time map 450 corresponding to the process 400 of FIG. 4A. Again, timing of system 100 within the context of map 450 is substantially similar to that described above with respect to time map 250. Accordingly, FIG. 4B employs the same reference numbers as FIG. 2B for that timing, which will not be separately discussed here. In particular, FIG. 4B illustrates possible infusion periods with respect the blood batch processing cycle. For example, an initial period 452 by medical treatment device 302 can occur before the first blood processing cycle and may overlap with at least the secondary fluid/drug flow 206 of the batch preparation stage of the blood processing cycle. Infusion may then be paused during blood withdrawal 208 of each batch preparation stage, and then resume at 454 during each blood treatment stage (constituted by blood treatment 216).

In some embodiments, infusion by medical treatment device 302 may again be paused during each batch return stage (constituted by blood infusion 224 and secondary fluid/drug flow 226) to allow system 100 sole access to vascular access 112. In other embodiments, infusion 458 by medical treatment device 302 may optionally continue during each batch return stage. In such embodiments, the rate of infusion 458 may be reduced as compared to infusion 454 during the blood treatment stage to accommodate the additional flow of blood from system 100 to the vascular access. The infusion may optionally resume (or increase to its nominal rate) for a period 456 during the secondary fluid/drug flow 206 of the next batch preparation stage.

Figure 5A:
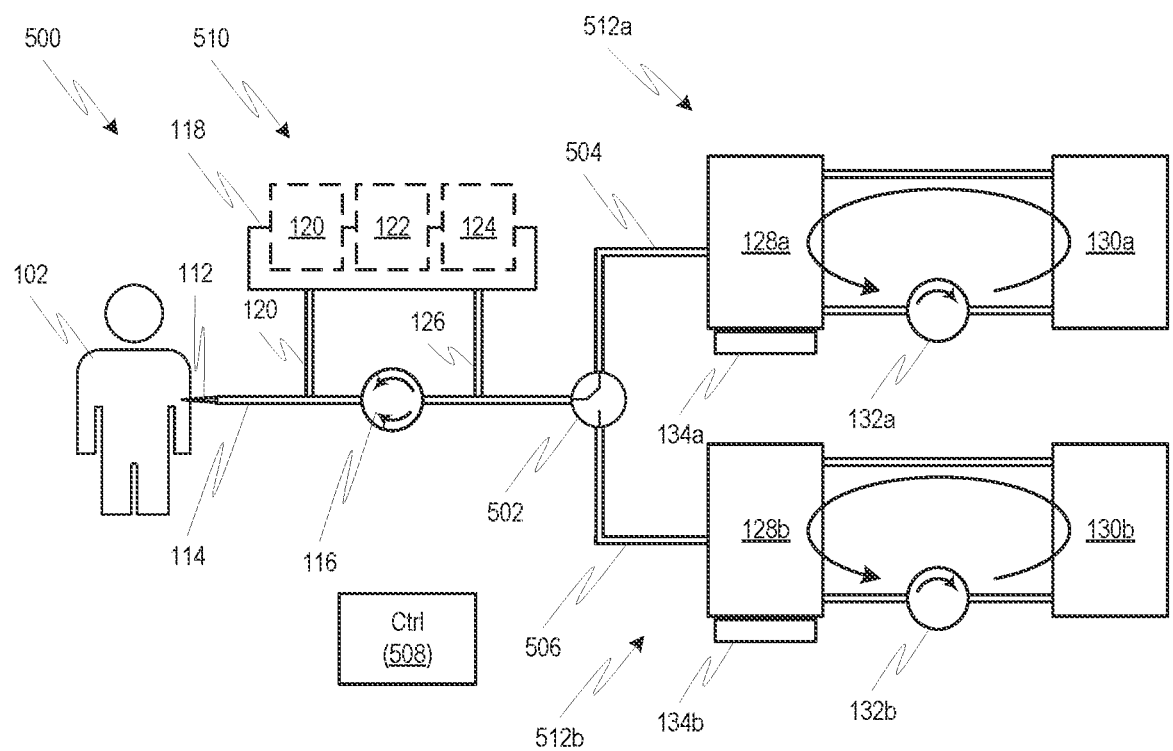
FIG. 5A is a simplified schematic diagram of a blood treatment system employing serial processing of multiple blood batches, according to one or more embodiments of the disclosed subject matter.

Although the description above has focused on the use of single blood reservoir 128, embodiments of the disclosed subject matter are not limited thereto. Indeed, in certain contemplated embodiments, extracorporeal blood treatment systems and methods can utilize more than one blood reservoir for serial or parallel treatment processing. For example, FIG. 5A shows a simplified layout for a generic extracorporeal blood treatment system 500 utilizing a pair of blood reservoirs 128a, 128b providing serial blood treatment processing. System 500 includes an interfacing circuit 510 and a pair of processing circuits 512a, 512b. Each processing circuit 512a, 512b can have respective blood reservoirs 128a, 128b, weight or fluid level sensors 134a, 134b, blood pumps 132a, 132b, which may be Harvard apparatuses and filtration devices 130a, 130b. Each processing circuit 512a, 512b is thus substantially similar to processing circuit 110 of FIG. 1A and may operate independently of each other to effect a blood treatment in a similar manner to processing circuit 110.

The interfacing circuit 510 is substantially similar to interfacing circuit 108 of FIG. 1A and thus may operate in a similar manner to interfacing circuit 108. However, interfacing circuit 510 further includes a fluid switch 502 (or combination of valves or other flow control devices to provide the effect of a switch) that connects single lumen conduit 114 to either an inlet conduit 504 of first processing circuit 512a or an inlet conduit 506 of second processing circuit 512b. Since only one processing circuit 512a, 512b can be connected to single lumen conduit 114 by switch 502 at a time, processing circuits 512a, 512b may be considered to operate serially.

For example, in FIG. 5A switch 502 selects for processing circuit 512a, such that blood or body fluid from patient 102 can be conveyed to reservoir 128a or processed blood from reservoir 128a can be returned to patient 102 via single lumen conduit 114 and inlet conduit 504. Meanwhile, processing circuit 512b is de-selected by switch 502. While de-selected, processing circuit 512b may recirculate previously withdrawn blood between reservoir 128b and filtration device 130b to effect a blood treatment. Thus, blood treatment processing by one of the processing circuits 512a, 512b may occur while the other of the processing circuits 512a, 512b is withdrawing or infusing blood, thereby taking advantage of what would otherwise be considered blood processing downtime in a single blood reservoir system. Alternatively, processing circuit 512b may be idle during the de-selected period. Similar to control system 142, control system 508 controls operation of components of the interfacing circuit 510 (for example, selection by switch 502) and processing circuits 512a, 512b. One of skill in the art will recognize that one or more additional processing circuit(s) are possible such as 512c, 512d, etc., by including additional switches.

Figure 5B:
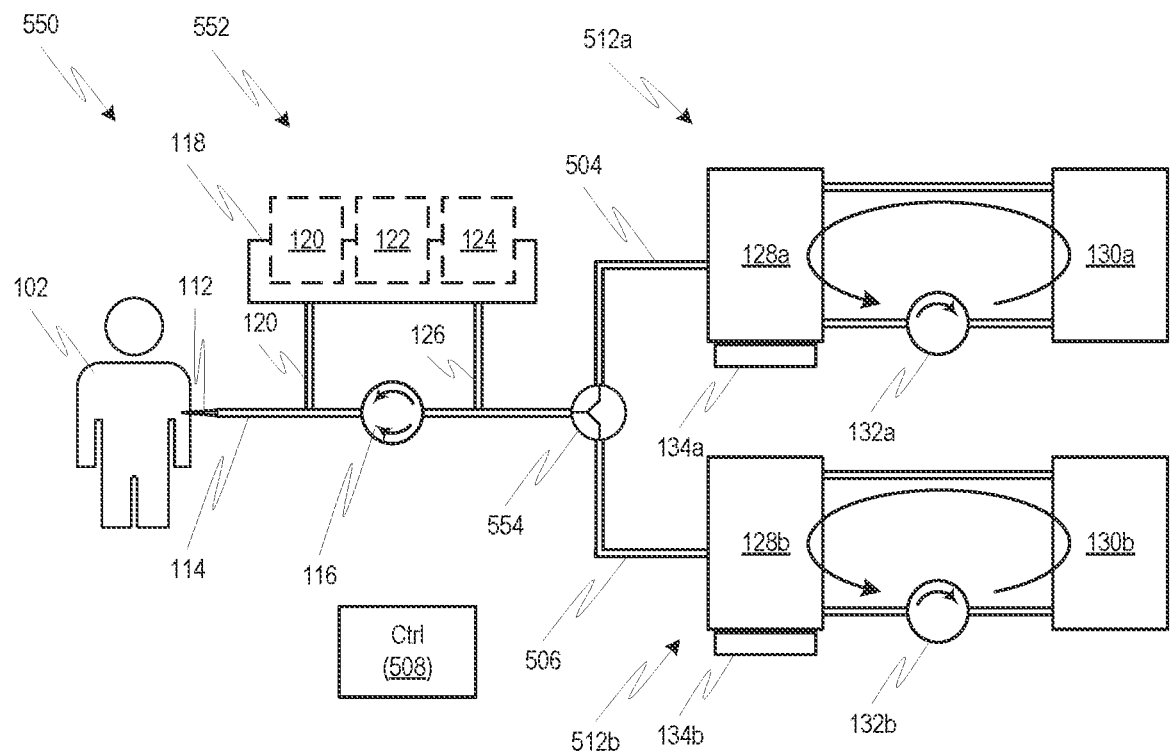
FIG. 5B is a simplified schematic diagram of a blood treatment system employing parallel processing of multiple blood batches, according to one or more embodiments of the disclosed subject matter.

In another example, FIG. 5B shows a simplified layout for a generic extracorporeal blood treatment system 550 utilizing a pair of blood reservoirs 128a, 128b providing parallel blood treatment processing. System 550 includes an interfacing circuit 552 and a pair of processing circuits 512a, 512b, each of which is substantially similar to processing circuit 110 of FIG. 1A and may operate independent of each other to effect a blood treatment in a similar manner to processing circuit 110.

The interfacing circuit 552 is similar to interfacing circuit 510 of FIG. 5A but includes a fluidic union 554 (or combination of valves or other flow control devices to provide the effect of a union) instead of a switch 502. The union 554 (e.g., a Y-connector) connects single lumen conduit 114 to both the inlet conduit 504 of first processing circuit 512a or the inlet conduit 506 of second processing circuit 512b. Since both processing circuits 512a, 512b are connected to single lumen conduit 114 by union 554 at a time, processing circuits 512a, 512b may be considered to operate in parallel. One of skill in the art will recognize that one or more additional processing circuit(s) are possible such as 512c, 512d, etc., by including additional unions.

For example, blood from patient 102 can be simultaneously conveyed to reservoirs 128a, 128b or processed blood from reservoirs 128a, 128b can be simultaneously returned to patient 102 via single lumen conduit 114 and inlet conduits 504, 506. As such, the blood volume from the patient 102 traveling along single lumen conduit 114 can be split between each of the blood reservoirs 128a, 128b, and blood returning from reservoirs 128a, 128b can be combined prior to introduction to patient at vascular access 112. Processing circuits 512a, 512b may also recirculate blood between reservoirs 128a, 128b and filtration devices 130a, 130b at the same time to effect a parallel blood treatment. Similar to control system 142, control system 508 controls operation of components of interfacing circuit 552 and processing circuits 512a, 512b.

Although processing circuits 512a, 512b are illustrated as being identical in FIGS. 5A-5B, in some embodiments, filtration devices 130a, 130b may be different (i.e., offering separate treatment modalities). For example, a first fraction of the withdrawn blood is subjected to a first treatment modality by processing circuit 512a while a second fraction of the withdrawn blood is subjected to a second treatment modality (which may be different or complementary to the first treatment modality or regimens) by processing circuit 512b. Moreover, although FIGS. 5A-5B illustrate exemplary systems with a pair of blood reservoirs, serial or parallel processing with additional blood reservoirs is also possible according to one or more contemplated embodiments. Indeed, the teachings of FIGS. 5A-5B can be readily extended to three or more blood reservoirs (and associated processing circuits) by appropriate design of switching (e.g., switch 502) or union (e.g., union 554) components. In some embodiments, a combination of serial and parallel processing circuits are contemplated.

Referring to FIGS. 6A-6I, operation of an exemplary extracorporeal blood treatment system 600 to provide hemodiafiltration (HDF) will be described. Hemodiafiltration (HDF) is a form of renal replacement therapy that utilizes convective clearance in combination with diffusive clearance. Compared with standard hemodialysis, HDF removes more middle-molecular-weight solutes. HDF system 600 can have a single-lumen conduit 606 connected to a single-lumen vascular access 604 coupled to the vascular system of patient 102. For example, the vascular access 604 can be a needle or catheter having size smaller than either 17 gauge or 7 French. A reversible blood pump 626 (e.g., pulsatile blood pump, peristaltic roller pump, withdrawal/infusion, etc.) is used to convey fluids along single-lumen conduit 606, e.g., blood to/from patient 102 and reservoir 634 or other fluids via supply lines 614, 629, 659, 661.

One or more sensors can be disposed along the flow path of the single-lumen conduit 606. For example, an air detector 608 can be disposed along the conduit 606 proximal to the vascular access 604 (viewed right to left) to detect any air that may be introduced into system 600 during the withdrawal for safety purposes. A pressure gauge 609 can also be provided along conduit 606 proximal to vascular access 604 to detect pressure changes during blood withdrawal or infusion, which changes may indicate, for example, decoupling of the vascular access 604 from the patient 102 or a blockage of the vascular access 604 or elsewhere along conduit 606.

One or more flow control devices can be disposed along the flow path of the single-lumen conduit 606. For example, a first valve 610 can be arranged along conduit 606 between the vascular access 604 and blood pump 626. In particular, first valve 610 may be located between connection points at conduit 606 for supply lines 614, 659 and the vascular access 604, so as to isolate the vascular access 604 when fluid is introduced to conduit 606 via these supply lines. A second valve 632 can be arranged along conduit 606 between blood pump 626 and blood chamber or reservoir 634, for example, to isolate the blood reservoir 634 from conduit 606 during blood processing. In particular, second valve 632 may be located between connection points at conduit 606 for supply lines 629, 661 and blood reservoir 634, so as to isolate the reservoir 634 when fluid is introduced to conduit 606 via these supply lines.

A supply 616 of hemofiltration (HF) fluid (e.g., substitution or replacement fluid) can be connected to supply lines 614 and 661, each of which may have a respective flow control device. For example, HF supply lines 614, 661 can have a third valve 612 and fourth valve 624, respectively, that opens/closes respective flow paths between the HF supply 616 and conduit 606. A heater 622 can heat HF fluid flowing along supply line 661 to ensure a temperature of HF fluid is appropriate for infusion into patient 102. A supply 620 of anticoagulant (e.g., heparin, citrate-based anticoagulants, nafamostat, epoprostenol, etc.) and a supply 630 of anticoagulant reversal agent (ARA) (e.g., protamine, calcium, etc.) can be connected to respective supply lines 659, 629, each of which may have a respective flow control device. For example, supply lines 659, 629 can have a fifth valve 618 and a sixth valve 628, respectively, that opens/closes respective flow paths between supplies 620, 630 and conduit 606. In particular, the connection point at conduit 606 for anticoagulant supply line 659 may be between the blood pump 626 and the connection point at conduit 606 for HF supply line 614, while the connection point at conduit 606 for ARA supply line 629 may be between the blood pump 626 and the connection point at conduit 606 for HF supply line 661. Together, the components arranged between and including the vascular access 604 and the second valve 632 may be considered an interfacing circuit of system 600. The remaining components of system 600 illustrated in FIG. 6A may be considered a processing circuit of system 600.

Blood reservoir 634 can have a first fluid port coupled to single lumen conduit 606, with access between the first fluid port and conduit 606 controlled by second valve 632. Blood reservoir 634 can also have a second fluid port coupled to recirculating supply line 638, with access between the second fluid port and supply line 638 controlled by a seventh valve 636. Blood reservoir 634 can also have a third fluid port coupled to recirculating return line 646, with access between the third fluid port and return line 646 controlled by an eighth valve 648. Although shown separate from blood reservoir 634, valves 632, 636, 648 (or other flow control components) may form part of the reservoir 634 itself in some embodiments. Moreover, in some embodiments, some of the valves for the blood reservoir 634 can be combined together or replaced by a common fluid control component providing similar functions, for example, where second valve 632 and seventh valve 636 are replaced by a fluidic switch that connects a fluid port of the blood reservoir to either conduit 606 or to recirculating supply line 638.

A blood pump 640 (e.g., pulsatile blood pump, peristaltic roller pump, Harvard apparatus, syringe pump, etc.) is used to convey fluids from reservoir 634 to dialyzer 644 (e.g., cross-flow dialyzer) via recirculating supply line 638 and from dialyzer 644 back to reservoir 634 via recirculating return line 646. In some embodiments, with utilization of a Harvard apparatus or syringe pump 640, recirculating return line 646 is no longer needed as conduit 630 is used to recirculate the fluid between blood reservoir 634 and dialyzer 644. A dialysate pump 652 (e.g., peristaltic pump, positive displacement pump, centrifugal pump, Harvard apparatus, syringe pump, etc.) is used to convey dialysate from a supply 656 to dialyzer 644, where the dialysate flows through a chamber of the dialyzer 644 separated by a membrane or filter from a chamber of the dialyzer 644 in which the blood flows. A heater 654 can heat dialysate flowing to dialyzer to ensure a temperature of dialysate compatible with the blood in reservoir 634. A separate pump 662 (e.g., peristaltic pump, positive displacement pump, centrifugal pump, etc.) can optionally be used to convey effluent (e.g., ultrafiltration fluid, removed solutes, and spent dialysate) from the dialyzer 644 to waste 658 (e.g., a waste container, drain, or other medical disposal).

Figure 7:
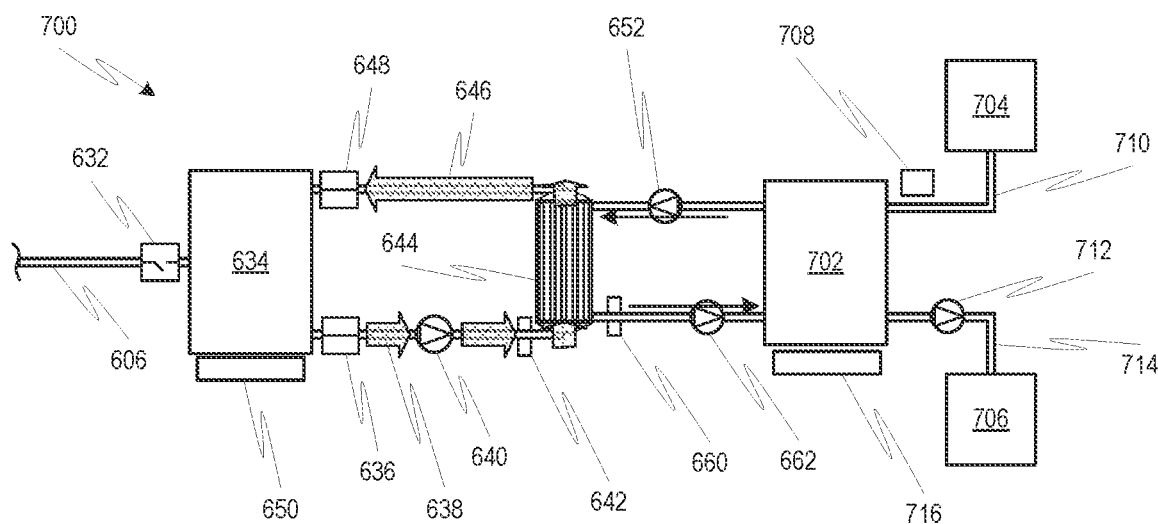
FIG. 7 illustrates a portion of the HDF system of FIG. 6A modified to employ dialysate recirculation, according to one or more embodiments of the disclosed subject matter.

Alternatively, dialysate pump 652 can pump dialysate from and effluent pump 662 can pump fluid to a common dialysate reservoir 702, for example, to provide recirculation of dialysate as shown in FIG. 7. Note that FIG. 7 only shows the components of the processing circuit 700, as the system components connected at the left end of conduit 606 would otherwise be the same as FIG. 6A. As shown in FIG. 7, a drain pump 712 can be connected to the common dialysate reservoir 702 to remove spent dialysate therefrom during or after processing, for example, by conveying spent dialysate to waste 706 via conduit 714. Dialysate supply 704 may thus be connected to the common dialysate reservoir 702 to provide fresh dialysate thereto during or before processing. A heater 708 may be supplied along dialysate supply line 710 for heating the fresh dialysate supplied to the reservoir 702. A weight sensor 716, similar to weigh sensor 650, or volume level sensor may be used to monitor a volume of fluid within dialysate reservoir 702.

Returning to FIG. 6A, one or more sensors can be disposed along the flow paths to/from dialyzer 644. For example, pressure gauge 642 can be disposed along conduit 638 distal to a blood inlet of dialyzer 644 (viewed right to left) to detect pressure changes during HDF processing, which changes may indicate, for example, a blockage of the dialyzer 644 or a blockage elsewhere along conduits 638, 646. For example, a blood leak detector 660 (e.g., optical detector) can be disposed proximal to an effluent outlet of dialyzer 644 to detect any blood that may have improperly crossed through a membrane/filter of the dialyzer 644.

Figure 6A:
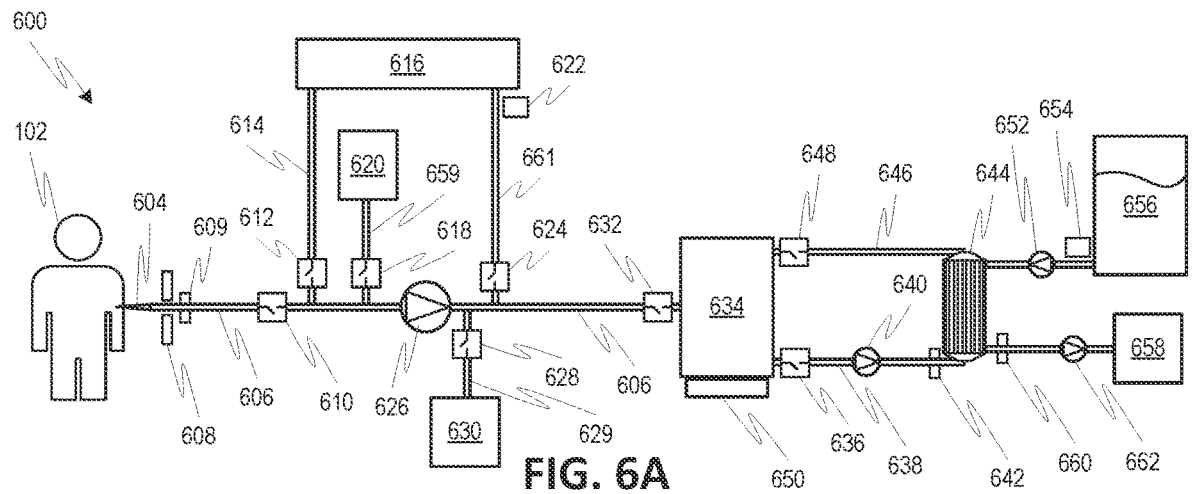
FIG. 6A illustrates an initial setup of a hemodiafiltration (HDF) system employing batch processing, according to one or more embodiments of the disclosed subject matter.
Figure 6B:
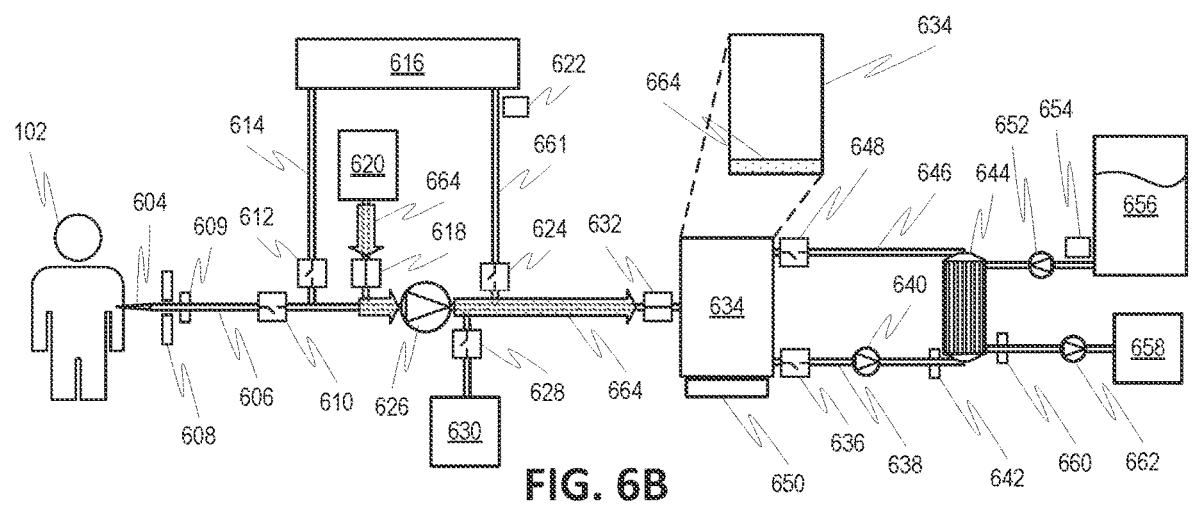
FIGS. 6B-6D illustrate the HDF system setup of FIG. 6A during anticoagulant fill, hemofiltration (HF) fluid fill, and blood fill stages, respectively.

At the start of a first cycle of the HDF treatment process, system 600 provides a volume of anticoagulant 664 to the blood reservoir 634, as shown in FIG. 6B. For example, fifth valve 618 and second valve 632 may be opened while the remaining valves 610, 612, 624, 628, 636, and 648 are closed. Pump 626 can operate in a first direction to convey the anticoagulant 664 from supply 620 along conduits 659 and 606 into reservoir 634. For example, when the anticoagulant 664 is heparin, the volume to be added to reservoir 634 may be 5-200 units of heparin per 100 ml of blood. If patient 102 has already been anticoagulated (i.e., by intravenous delivery of an appropriate anticoagulant), the system may skip providing anticoagulant 644 and instead proceed directly to the configuration of FIG. 6C.

Figure 6C:
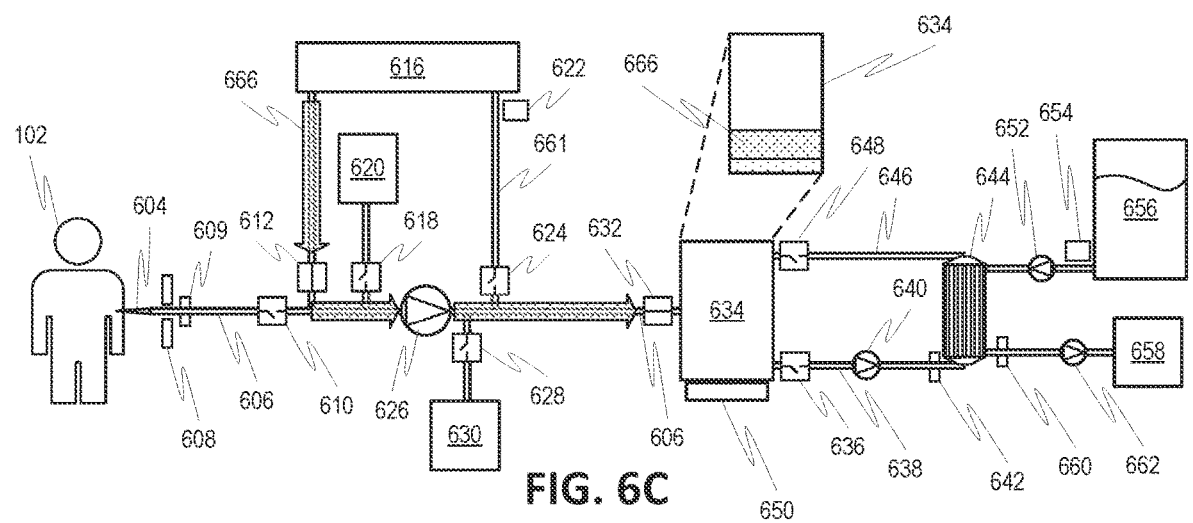

After addition of anticoagulant 644 in FIG. 6B, the system 600 provides a volume of HF fluid 666 to the blood reservoir, as shown in FIG. 6C. For example, third valve 612 and second valve 632 may be opened while the remaining valves 610, 618, 624, 628, 636, and 648 are closed. Pump 626 can operate in the first direction to convey the HF fluid 666 from supply 616 along conduits 614 and 606 into reservoir 634. For example, the volume of HF fluid 666 may be determined based on the volume of blood to be added to reservoir 634 and the expected volume of ultrafiltrate generated during processing.

Figure 6D:
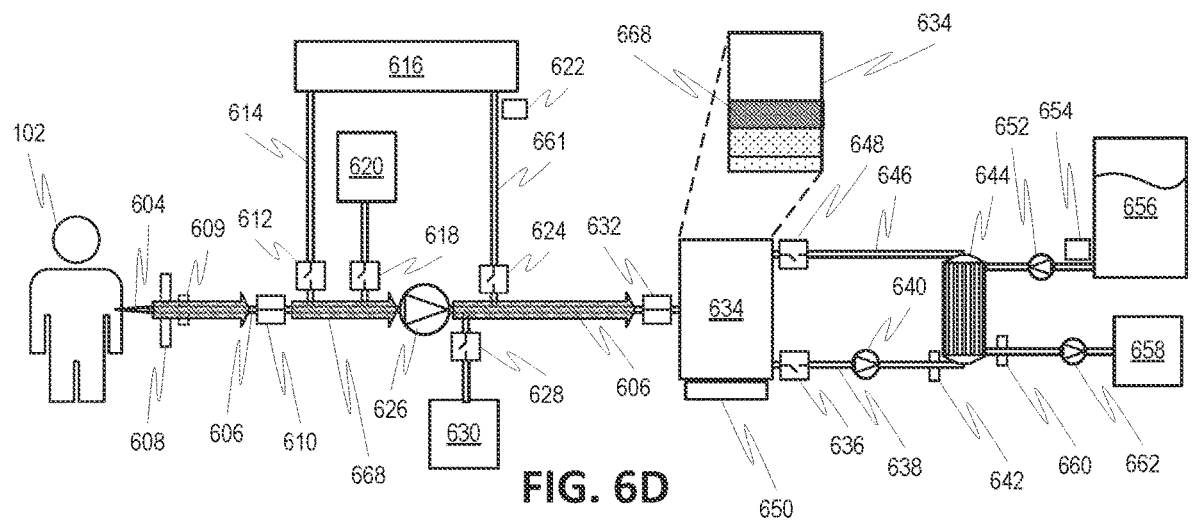

After addition of HF fluid 666 in FIG. 6C, the system 600 withdraws a volume of blood 668 from the patient 102 and adds it to blood reservoir 634, as shown in FIG. 6D. For example, first valve 610 and second valve 632 may be opened while the remaining valves 612, 618, 624, 628, 636, and 648 are closed. Pump 626 can operate in the first direction to convey blood from the patient 102 via vascular access 604 along conduit 606 into reservoir 634. For example, the volume of blood 668 may be determined based on the total blood volume of the patient, available capacity of the reservoir 634, a timing of each processing cycle, and/or maximum withdrawal flow rates based on size of vascular access 604 and/or size of conduit 606. For example, the volume of blood 668 may be 10-300 ml or 2-7% of the total blood volume of patient 102. Weight sensor or other volume level sensor 650, which may have an accuracy of 1 gram or better or 1 ml or better, can be used to monitor a volume of the blood that has been added to reservoir 634. Note that FIGS. 6B-6D show fluid volumes 664, 666, and 668 as being a lamination of volumes for illustration and discussion purposes only. In practical implementations, the anticoagulant, HF fluid, and blood would all mix together within reservoir 634 to provide a single mixed volume or an admixture, for example, as illustrated by 670 in FIG. 6E.

Figure 6E:
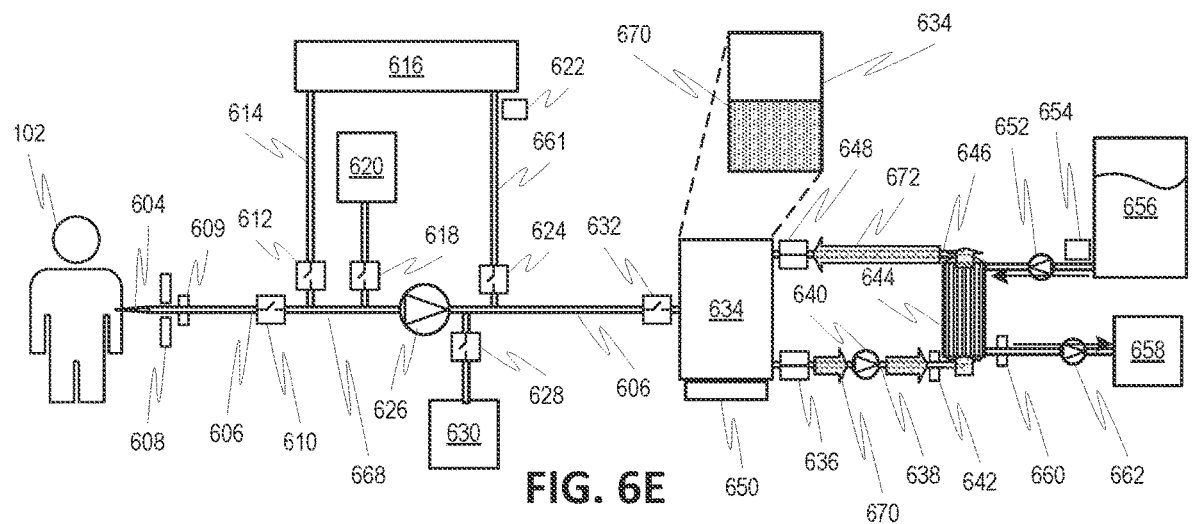
FIGS. 6E-6F illustrate the HDF system setup of FIG. 6A during and after processing to perform an HDF treatment on the blood, respectively.

After addition of blood 668 in FIG. 6D, the system 600 may shift to the blood processing stage of the treatment cycle. For example, FIG. 6E illustrates system 600 at the start of treatment processing, where the initial blood/HF fluid/anticoagulant mixture 670 is circulated through dialyzer 644 to yield processed blood 672. For example, seventh valve 636 and eighth valve 648 may be opened while the remaining valves 610, 612, 618, 624, 628, and 632 are closed. Pump 640 can convey the blood mixture 670 from reservoir 634 along recirculation supply line 638 to and through dialyzer 644 and then back to reservoir 634 along recirculation return line 646. For example, the flow rate provided by pump 640 may be 50-500 ml/min or more (e.g., 750 ml/min). At the same time, dialysate pump 652 can convey dialysate from supply 656 to dialyzer 644 and an effluent pump 662 can withdraw effluent from dialyzer 644 to waste 658.

Pump 640 can convey the blood mixture 670 at a flow rate that is greater, for example, at least 1.25 times greater, than a withdrawal rate of the blood from patient in FIG. 6C. For example, the withdrawal rate may be less than 200 ml/min, such as 100-150 ml/min, while the flow rate provided by pump 640 in FIG. 6E may be at least 300 ml/min. Dialysate pump 652 and/or effluent pump 662 can generate a flow rate of dialysate through dialyzer 644 that is equal to or greater than the flow rate of the blood mixture 670 through the dialyzer 644. For example, the flow rate of dialysate through dialyzer 644 may be at least 500 ml/min, or 500 ml to 1500 ml/min.

The recirculation of blood 670 between reservoir 634 and dialyzer 644 in FIG. 6E may continue until an appropriate stop or end condition is reached. For example, weight sensor or volume level sensor 650 can monitor a weight or volume of fluid within reservoir 634 (e.g., dynamically during recirculation or during intermittent pauses in recirculation) to determine when sufficient waste fluid has been removed by the dialyzer 644. Alternatively or additionally, recirculation may continue for a predetermined time or until blood 670 has passed through the dialyzer 644 for a predetermined number of times. For example, for a 300 ml initial blood volume, recirculation may continue for less than or equal to 3 minutes or until the entire initial blood volume has passed through the dialyzer 644 at least three times.

Since the same blood can be reprocessed by the dialyzer 644 multiple times rapid clearance of solutes and ultrafiltration (as needed) can be achieved. Further since blood flow rate through the dialyzer 644 in FIG. 6E can be greater than the blood withdrawal in FIG. 6D (otherwise limited by the small size of the vascular access 604 and/or single-lumen conduit 606), the clearance of solutes and ultrafiltration can be further improved, including clearance of middle molecules. In other words, system 600 takes advantage of the decoupling of blood processing flow rate from blood withdrawal flow rate to allow for a singular vascular access of smaller size than conventional RRT systems while achieving treatment performance comparable to or even better than conventional RRT systems.

Figure 6F:
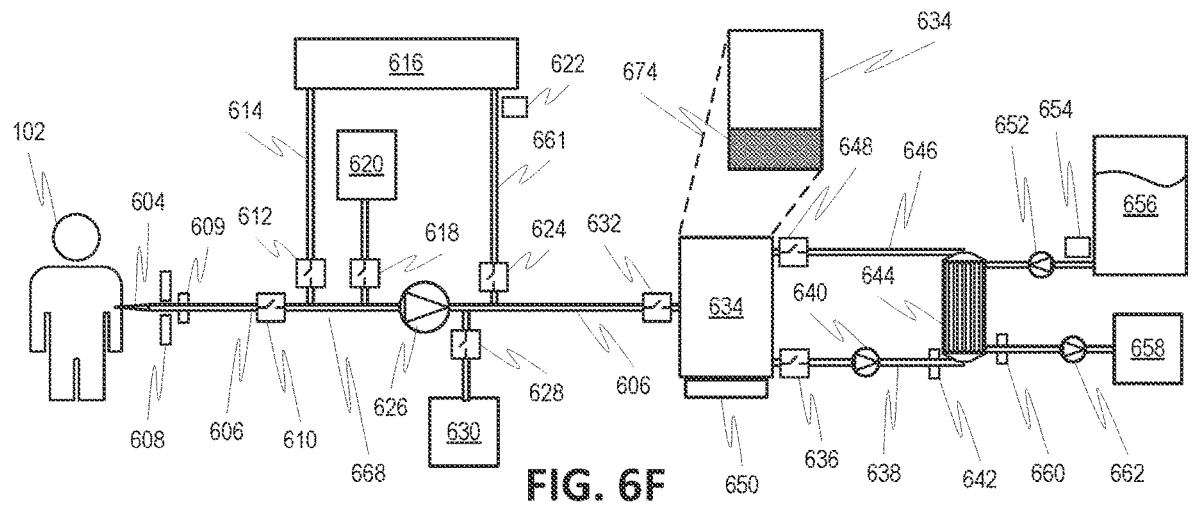

Once the end condition has been reached, system 600 may shift to the blood return stage of the treatment cycle. For example, FIG. 6F illustrates system 600 at the end of treatment processing, where the final processed blood 674 after recirculation awaits in blood chamber 634 for infusion to patient 102. For example, valves 636, 648 may be closed and pump 640 stopped to terminate recirculation. Dialysate pump 652 and effluent 662 may also be stopped at the same time, or a short time thereafter. Other valves may also be closed, for example, to allow blood 674 to temporarily settle to provide an accurate weight measurement by sensor 650 prior to infusion.

Figure 6G:
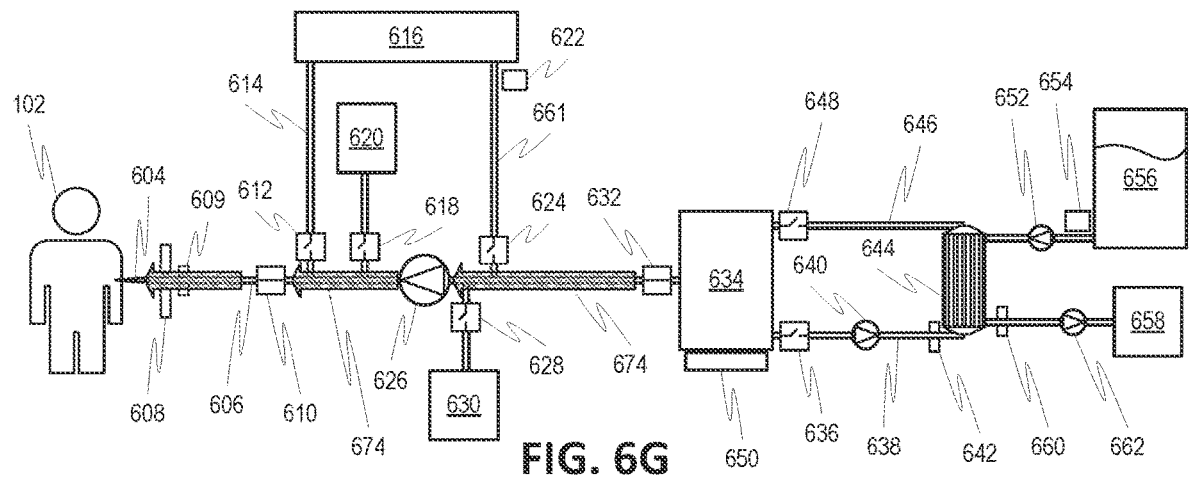
FIGS. 6G-6I illustrate the HDF system setup of FIG. 6A during blood return, anticoagulant reversal agent infusion, and HF fluid flush stages, respectively.

In FIG. 6G, the system 600 infuses the processed blood 674 from reservoir 634 back to patient 102. For example, first valve 610 and second valve 632 may be opened while the remaining valves 612, 618, 624, 628, 636, and 648 are closed. Pump 626 can operate in a second direction (opposite to the first direction) to convey processed blood 674 along conduit 606 from reservoir 634 to patient 102 via vascular access 604. For example, pump 626 may infuse the processed blood 674 at a flow rate that is the same or substantially the same as the previous withdrawal rate in FIG. 6C. For example, the infusion rate may be less than 200 ml/min, such as 100-150 ml/min or 25 ml/min, 50 ml/min, 100 ml/min, or 150 ml/min.

Figure 6H:
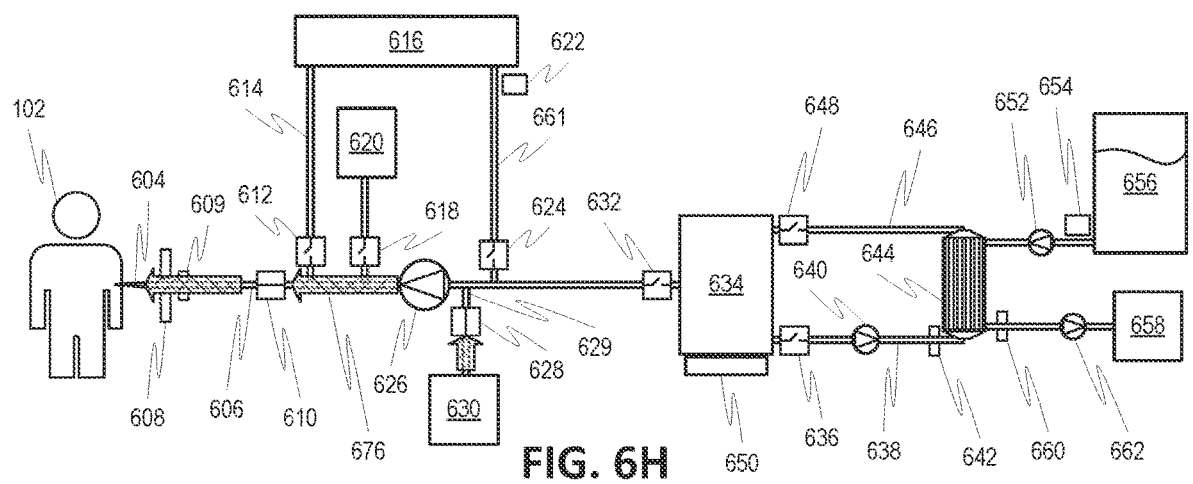

After infusion of processed blood 674 in FIG. 6G, the system 600 can infuse a volume of ARA 676 into patient 102, as shown in FIG. 6H. For example, first valve 610 and sixth valve 628 may be opened while the remaining valves 612, 618, 624, 632, 636, and 648 are closed. Pump 626 can operate in the second direction to convey ARA 676 from ARA supply 630 along conduits 629, 606 and into patient 102 via vascular access 604. For example, the volume of ARA 676 may be determined based on the processed blood volume 674 returned to the patient, the amount of anticoagulant added at FIG. 6B, and/or the type of ARA and anticoagulant.

Figure 6I:
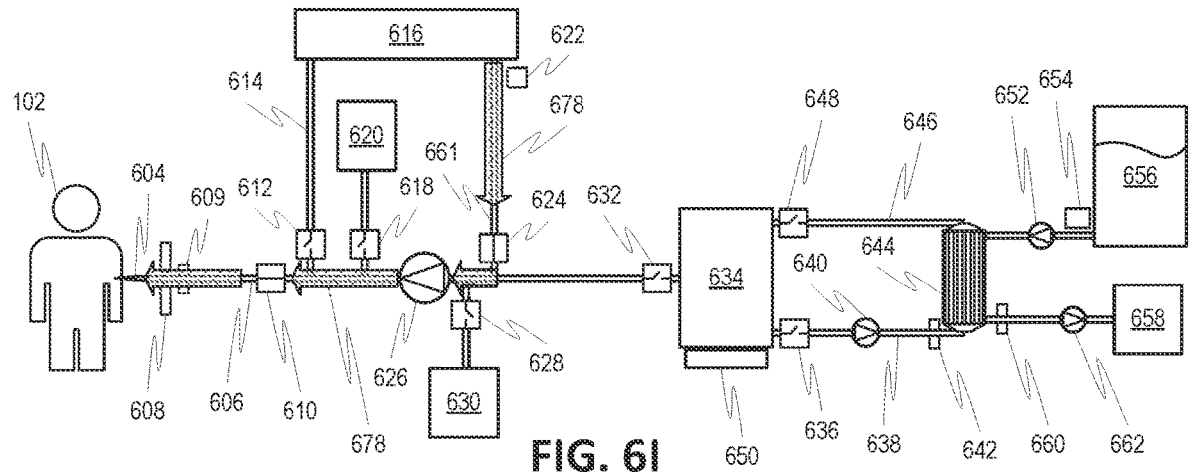

After infusion of ARA 676 in FIG. 6H, the system 600 can infuse a volume of HF fluid 678 into patient 102, as shown in FIG. 6I. For example, first valve 610 and fourth valve 624 may be opened while the remaining valves 612, 618, 628, 632, 636, and 648 are closed. Pump 626 can operate in the second direction to convey the HF fluid from HF supply 616 along conduits 661, 606 and into patient 102 via vascular access 604. The infusion of HF fluid 678 may be effective to flush conduit 606 in preparation for the next batch processing cycle. Thus, the system can return to the configuration of FIG. 6B to process the next blood batch from patient 102 or may otherwise terminate if no further batches are desired.

Although the discussion above of system 600 in FIGS. 6A-6I specifically describe an HDF treatment process, system 600 may also provide a hemodialysis (HD) treatment process. However, instead of supply 616 providing HF fluid, it can provide a flushing fluid, such as normal saline (NS), etc. Since there is no or little convective flow through the membrane of the dialyzer 644 in an HD treatment setup, the volume of flushing fluid may be less than that of HF fluid used at FIGS. 6C, 6I. For example, the volume of flushing fluid may be just enough to clear conduit 606 of any prior flows of anticoagulant (at FIG. 6B) or ARA (at FIG. 6H). In the HD treatment setup, the blood flow rate through dialyzer 644 may be less than that at FIG. 6E in the HDF treatment setup. The type of dialyzer may also be different from dialyzer 644 in the HDF treatment setup. The configuration and operation of system 600 to provide an HD treatment would otherwise be similar to that illustrated in FIGS. 6A-6I.

Figure 8:
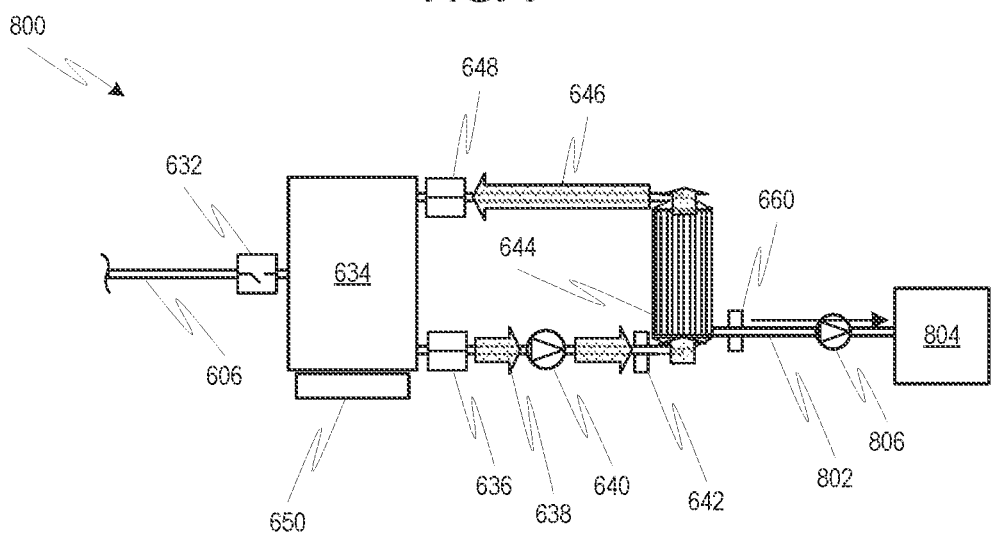
FIG. 8 illustrates a portion of a hemofiltration (HF) system during a processing stage to perform an HF treatment on a batch of blood, according to one or more embodiments of the disclosed subject matter.

As referenced above, embodiments of the disclosed systems can be readily modified to provide other treatment modalities by swapping out one treatment module for another while maintaining other components of the system (e.g., the primary module). For example, the HDF system 600 of FIG. 6A-6I can be modified to provide an HF treatment, as illustrated in FIG. 8. Note that FIG. 8 only shows the components of the processing circuit 800, as the system components connected at the left end of conduit 606 would otherwise be the same as FIG. 6A. As illustrated in FIG. 8, processing circuit 800 removes the dialysate pump 652, heater 654, and dialysate supply 656 from the setup of system 600, instead relying on drain pump 806 to pull waste effluent from dialyzer 644 along drain line 802 to waste 804. Operation of processing circuit 800 may otherwise be substantially the same as that illustrated in FIGS. 6A-6I.

Figure 9:
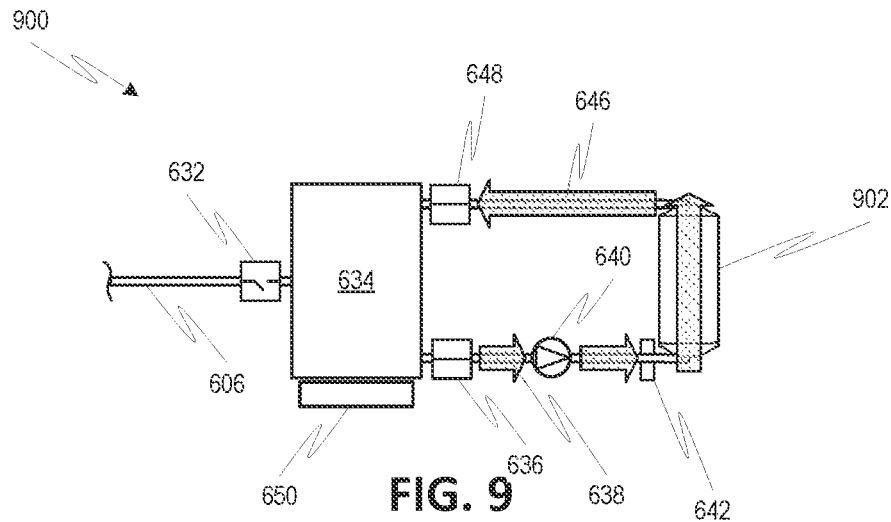
FIG. 9 illustrates a portion of a hemoperfusion (HPF) system during a processing stage to perform an HPF treatment on a batch of blood, according to one or more embodiments of the disclosed subject matter.

In another example, the HDF system 600 of FIG. 6A-6I can be modified to provide an HPF treatment, as illustrated in FIG. 9. Note that FIG. 9 only shows the components of the processing circuit 900, as the system components connected at the left end of conduit 606 would otherwise be the same as FIG. 6A. As illustrated in FIG. 9, processing circuit 900 of the HPF system replaces dialyzer 644 of HDF system 600 with an HPF cartridge or device 902. Since HPF relies on absorption of waste products to particles rather than diffusion or convection across a membrane into flowing dialysate, the processing circuit 900 of the HPF system also removes all components related to dialysate flow from the setup of FIG. 6A, e.g., dialysate pump 652, heater 654, dialysate supply 656, leak detector 660, effluent pump 662, and waste 658. Operation of processing circuit 900 may otherwise be substantially the same as that illustrated in FIGS. 6A-6I.

In certain instances, the filter or filtration device can be for example, an extracorporeal hemoadsorption filter device to remove cytokines from circulating blood such as a biocompatible, sorbent bead technology e.g., CytoSorb™, CytoSorbents™, Inc. CytoSorb hemoadsorption beads are polystyrene-divinylbenzene porous particles (450 μm avg. particle diameter, 0.8-5 nm pore diameter, 850 $m^2$/g surface area) with a biocompatible polyvinyl-pyrrolidone coating. See for example, U.S. Pat. No. 8,647,666 which claims a method of using a composition comprising polystyrene divinyl benzene copolymer and a polyvinyl pyrrolidone polymer.

In certain other instances, the filter or filtration device is Seraph® Microbind® Affinity Blood Filter, which is a filter that allows body fluids to pass over microbeads coated with molecular receptor sites that mimic the receptors on human cells which pathogens use to colonize when they invade the body. The adsorption media is a flexible platform that uses covalently-bonded, immobilized heparin or heparan sulfate for its unique binding capacity. See, for example, U.S. Pat. No. 8,758,286 or U.S. Pat. No. 9,173,989, disclosing at least one polysaccharide adsorbent, or immobilized heparin.

Dose, Intravenous Access, and Anticoagulation Considerations

In general, the cycle time and therefore total dose of RRT requires an adequate intravenous access. A standard double-lumen dialysis catheter of 11 Fr (each lumen of 5-5.5 Fr) can run a blood flow rate (Qb) of 200-300 ml/min. Thus, a single lumen catheter of at least 5 Fr can easily allow batches of 200-250 ml to be drawn into the SLAMB in 1 minute and returned in 1 minute. Single pass urea clearance in hemodialysis ranges between 85-90%, thus a batch of 200-250 ml can then be (re)cycled at 200-400 ml/min within the reservoir for 2-3 minutes to achieve 90-95% clearance (See, Macias et al., Clin Kidney J, 12: 447-455, 2019). Therefore, a conservative estimate of the total cycle time with a single-lumen catheter of 7 Fr is as follows: 5 minutes (1 minute ingress, 2-3 minutes of clearance, 1 minute blood return), which would allow 12-15 cycles per hour. If the urea distribution is assumed to be the same as total body water, the standard CRRT dose 20 ml/kg/hr equates to a Kt/V of 0.8 (See, Vijayan et al. Am J Kidney Dis, 59: 569-576, 2012). Modeling of different SLAMB prescriptions are shown in Table 1. In the above example, a 75 kg patient dosed with a SLAMB prescription of 200 ml batch, 5-minute cycle time, 0 ml of ultrafiltrate would achieve a Kt/V of 0.8 in 14.8 hours. If smaller/longer intravenous access where utilized thus extending the cycle time, the time to achieve a Kt/V would be extended. In this example, if the ingress/egress of blood from the device were extended to 9 minutes (3 minutes cycling, 3 minutes for ingress and 3 minutes for egress) a catheter would need to perform a Qb flow of at least 67 ml/min and a Kt/V of 0.8 is achieved in 24 hours.

Since the SLAMB system utilizes small batches that are resident in a reservoir, some element of anticoagulation may be required.

TABLE 1

SLAMB Dosing Models Based on Various Prescriptions

| Batch Size (ml) | Total Cycle Time (minutes) | Reservoir Cycle Time (minutes) | Time to Achieve Dose of 20 cc/kg/HR (hours) | IV Access Minimum Flow Rate Requirement (ml/min) |
|---|---|---|---|---|
| 166 ml | 3 | 2 | 17.9 | 200 |
| 100 ml | 3.5 | 2 | 20.8 | 133 |
| 100 ml | 4 | 2 | 23.8 | 100 |
| 150 ml | 4 | 2 | 15.9 | 150 |
| 150 ml | 4 | 2.5 | 15.9 | 200 |
| 150 ml | 5 | 2.5 | 19.8 | 120 |
| 150 ml | 6 | 2.5 | 23.8 | 85.7 |
| 200 ml | 4 | 3 | 11.9 | 400 |
| 200 ml | 5 | 3 | 14.8 | 200 |
| 200 ml | 6 | 3.5 | 17.8 | 160 |
| 200 ml | 7 | 3.5 | 20.8 | 114 |
| 200 ml | 3 | 2 | 8.9 | 400 |
| 250 ml | 3.5 | 2 | 8.3 | 400 |
| 250 ml | 5 | 3 | 11.8 | 250 |
| 250 ml | 6 | 4 | 14.2 | 250 |
| 250 ml | 7 | 4 | 16.6 | 167 |
| 300 ml | 6 | 4 | 11.8 | 300 |
| 300 ml | 7 | 4 | 13.8 | 200 |
| 300 ml | 8 | 4 | 15.7 | 150 |

TABLE 2

SLAMB Dose Modeling

| Weight (kg) | Batch Size (ml) | Cycle Number | Baseline BUN (mg/dl) | Urea Clearance | New BUN (mg/dl) | Cycle Time (minutes) | Total Time |
|---|---|---|---|---|---|---|---|
| 75 | 150 | 1 | 100 | 95% | 99.6833333 | 4 | 4 |
| 75 | 150 | 2 | 99.6833333 | 95% | 99.3676694 | 4 | 8 |

TABLE 2-continued

SLAMB Dose Modeling

| Weight (kg) | Batch Size (ml) | Cycle Number | Baseline BUN (mg/dl) | Urea Clearance | New BUN (mg/dl) | Cycle Time (minutes) | Total Time |
|---|---|---|---|---|---|---|---|
| 75 | 150 | 3 | 99.3676694 | 95% | 99.0530052 | 4 | 12 |
| 75 | 150 | 4 | 99.0530052 | 95% | 98.7393373 | 4 | 16 |
| 75 | 150 | 5 | 98.7393373 | 95% | 98.4266627 | 4 | 20 |
| 75 | 150 | 6 | 98.4266627 | 95% | 98.1149783 | 4 | 24 |
| 75 | 150 | 7 | 98.1149783 | 95% | 97.8042809 | 4 | 28 |

Model progresses until target BUN is achieved

Legend: TBW=total body water; BUN=blood urea nitrogen; $C_0$=Baseline BUN

Equations $$\text{New } BUN = \frac{C_0 * [TBW - (\text{Batch size [liters]} * \text{Clearance [\%]})]}{TBW}$$

TBW=weight (kg)*0.6 (liters)

In other aspects, the SLAMB system includes additional embodiments. For example, the SLAMB system can be used to infuse blood products into a patient. This is direct infusion of blood, platelets, and other blood products or blood-like components into a patient. These are blood products properly screened, which do not need to be further processed with hemoperfusion.

In other aspects, the SLAMB system can be used to process freshly donated blood and infuse the blood into a patient. This allows for emergency transfusions where pre-screened whole blood is not available (i.e. battlefield scenarios, austere environments, mass casualty situations.) In these scenarios, the 'walking blood bag' or donor donates fresh blood. The blood is then processed through filtration (e.g., a Seraph® cartridge from ExThera Medical, Martinez California; http://www.extheramedical.com/exthera-seraph) to reduce potential pathogens prior to infusion into a patient.

In other aspects, the SLAMB system can further include adding the ability to provide IV fluids and IV drugs. If the pump is hooked up to a central line that is normally used for injecting fluids or drugs, the pump will still allow for the infusion of these products during use.

Conclusion

A SLAMB-HDF allow RRT to be conducted with a single and small vascular access. Systems based on this design are simpler than current RRT systems which make them less expensive, lighter, and more portable thus increasing the options for patients who require RRT.

It will be appreciated that the aspects of the disclosed subject matter, for example, the control systems 142, 508, the input/output 144, the control of the systems illustrated in FIGS. 6A-9, and/or processes 200, 400, can be implemented, fully or partially, in hardware, hardware programmed by software, software instruction stored on a computer readable medium (e.g., a non-transitory computer readable medium), or any combination of the above. For example, components of the disclosed subject matter, including components such as a control unit, controller, processor, user interface, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

EMBODIMENTS

Embodiment 1: A blood treatment method comprising:
(a) conveying a volume of blood via a first conduit from a vascular access of a patient to a blood chamber at a first flow rate, the first conduit having only a single lumen;
(b) conveying the blood from the blood chamber through a filtration device at a second flow rate to perform an extracorporeal treatment on the blood and returning the treated blood to the blood chamber; and
(c) returning the blood from the blood chamber to the vascular access of the patient at a third flow rate via the first conduit, wherein the second flow rate is decoupled from both the first and third flow rates.

Embodiment 2: The method of embodiment 1, wherein the first conduit is a needle or cannula forming at least part of the vascular access.

Embodiment 3: The method of embodiment 2, wherein the catheter or needle of the first conduit has a size of either 2-11 French or 10-23 gauge.

Embodiment 4: The method of any one of embodiments 1-3, wherein the vascular access comprises multiple lumens, and the first conduit is coupled to respective outlets of one or more of the multiple lumens.

Embodiment 5: The method of any one of embodiments 1-4, wherein the extracorporeal treatment is at least one of hemodialysis, hemofiltration, hemodiafiltration, or hemoperfusion.

Embodiment 6: The method of any one of embodiments 1-5, wherein the volume of blood is 2-7%, inclusive, of a total blood volume of the patient.

Embodiment 7: The method of any one of embodiments 1-6, wherein the second flow rate is 50 ml/min-500 ml/min, inclusive.

Embodiment 8: The method of embodiment 7, wherein the second flow rate is at least 300 ml/min.

Embodiment 9: The method of any one of embodiments 1-8, wherein (b) is repeated such that the blood is recirculated more than once through the filtration device via the blood chamber.

Embodiment 10: The method of any one of embodiments 1-9, wherein the second flow rate is greater than both the first and third flow rates.

Embodiment 11: The method of embodiment 10, wherein the second flow rate is at least 1.25 times greater than either of the first flow rate or third flow rate.

Embodiment 12: The method of any one of embodiments 1-11, wherein (b) is such that middle molecules contained in the blood are removed via the filtration device.

Embodiment 13: The method of embodiment 12, wherein:
the first conduit comprises a single-lumen catheter or needle having a size smaller than either 7 French or 17 gauge, and beta 2 microglobulin clearance is at least 100 ml/min.

Embodiment 14: The method of any one of embodiments 1-13, further comprising monitoring a weight of the blood chamber or a volume level of the blood chamber and correlating the monitored weight to a stage of the dialysis process.

Embodiment 15: The method of embodiment 14, wherein the monitoring occurs simultaneously with the conveying of (b).

Embodiment 16: The method of embodiment 14, wherein the monitoring occurs during a temporary pause in the conveying of (b).

Embodiment 17: The method of embodiment 14, wherein the monitoring is via a gravity scale having an accuracy of 1 g or less.

Embodiment 18: The method of any one of embodiments 1-17, comprising, prior to (b), adding a first volume of supplemental fluid and/or adding a second volume of anticoagulant to the blood chamber.

Embodiment 19: The method of embodiment 18, wherein the supplemental fluid comprises a hemofiltration fluid, or a normal saline (NS) or other flushing fluid.

Embodiment 20: The method of embodiment 18, wherein:
the anticoagulant is one or more of heparin, citrate-based anticoagulant, nafamostat, and epoprostenol, and/or the anticoagulant included heparin, and a ratio of the second volume to the withdrawn blood volume is 5-200 units of heparin to 100 ml of blood.

Embodiment 21: The method of any one of embodiments 1-20, comprising, during (b), adding a third volume of supplemental fluid and/or adding a fourth volume of anticoagulant reversal agent to the returning blood.

Embodiment 22: The method of embodiment 21, wherein the supplemental fluid comprises a hemofiltration fluid, or a normal saline (NS) or other flushing fluid.

Embodiment 23: The method of embodiment 21, wherein the third volume, the fourth volume, or a combination of the third and fourth volumes is 1-100 ml.

Embodiment 24: The method of any one of embodiments 1-23, wherein (b) comprises flowing a dialysate through the filtration device on a side of a filter opposite from the blood.

Embodiment 25: The method of embodiment 24, wherein a flow rate of the dialysate is at least 500 ml/min.

Embodiment 26: The method of any one of embodiments 1-25, wherein between (a) and (c), (b) is repeated such that blood is continuously recirculated at the second flow rate through the filtration device in a single flow direction.

Embodiment 27: The method of any one of embodiments 1-26, wherein (a) comprises conveying a first portion of the blood from the first conduit into the blood chamber and conveying a second portion of the blood from the first conduit into another blood chamber;
wherein (b) further comprises conveying the blood from the another blood chamber to another filtration device and returning the treated blood from the another filtration device to the another blood chamber; and wherein (c) comprises returning the blood from the blood chamber and the another blood chamber to the vascular access of the patient via the first conduit.

Embodiment 28: The method of any one of embodiments 1-27, further comprising:
infusing a fluid or drug into the patient via the first conduit and the vascular access, and interrupting the infusing during at least (a).

Embodiment 29: The method of embodiment 28, wherein the infusing occurs simultaneously with (b).

Embodiment 30: The method of embodiment 28, wherein the infusing occurs simultaneously with or after (c).

Embodiment 31: The method of any one of embodiments 1-30, wherein (a) comprises using a blood pump disposed in a flowpath between the vascular access and the blood chamber to convey the blood along the first conduit, the blood pump operating in a first direction; and
wherein (c) comprises using the blood pump to return the blood to the vascular access of the patient, the blood pump operating in a second direction opposite to the first direction.

Embodiment 32: The method of any one of embodiments 1-31, wherein (b) comprises using a blood pump disposed in a flowpath between the blood chamber and the filtration device to convey the blood, the blood pump operating in a single direction.

Embodiment 33: The method of any one of embodiments 1-32, after (c), repeating (a)-(c) on another volume of blood from the patient.

Embodiment 34: The method of any one of embodiments 1-33, wherein a time to perform (a)-(c) is less than or equal to 10 minutes.

Embodiment 35: The method of embodiment 34, wherein a time to perform (b) is less than or equal to 3 minutes.

Embodiment 36: A blood treatment system comprising:
a processing fluid circuit having a reservoir, a first blood pump, and a filtration device, an inlet of the reservoir being coupled to a blood outlet of the filtration device and an outlet of the reservoir being coupled to a blood inlet of the filtration device such that blood from the reservoir is recirculated through the filtration device in a first direction via the first blood pump;
an interfacing fluid circuit having a first conduit coupled to the reservoir and a second blood pump, the first conduit having only a single lumen, the second blood pump being switchable between a first operation mode where a batch of blood is conveyed from a vascular access of a patient via the first conduit and a second operation mode where blood from the reservoir is conveyed to the vascular access via the first conduit for infusion into the patient; and a controller configured to control operation of the first and second blood pumps in performing an extracorporeal treatment on the batch of blood from the patient.

Embodiment 37: A blood treatment system comprising:
- a reservoir for holding a batch of blood from a patient;
- a first conduit for conveying blood from a vascular access of the patient during a first stage and for returning treated blood to the vascular access during a third stage, the first conduit having only a single lumen;
- a filter for performing extracorporeal treatment on blood passing therethrough by removing waste molecules and/or fluid;
- a recirculating blood processing loop connecting the reservoir to the filter;
- a first blood pump for conveying blood in the recirculating blood processing loop; and
- a controller configured to control the first blood pump to repeatedly recirculate blood from the reservoir through the filter during a second stage between the first and third stages.

Embodiment 38: The system of any one of embodiments 36-37, wherein the extracorporeal treatment is at least one of hemodialysis, hemofiltration, hemodiafiltration, or hemoperfusion.

Embodiment 39: The system of any one of embodiments 36-38, wherein the first conduit is a needle or cannula forming at least part of the vascular access.

Embodiment 40: The system of embodiment 39, wherein the catheter or needle of the first conduit has a size of either 2-11 French or 10-23 gauge.

Embodiment 41: The system of one of embodiments 36-38, wherein the vascular access comprises multiple lumens, and the first conduit is coupled to respective outlets of the multiple lumens by a Y-connector.

Embodiment 42: The system of any one of embodiments 36-41, wherein the reservoir has a volume of 10-300 ml, inclusive.

Embodiment 43: The system of any one of embodiments 36-42, wherein the controller controls the first blood pump to generate a flow rate of blood in the processing fluid circuit or in the recirculating blood processing loop that is 50-500 ml/min, inclusive.

Embodiment 44: The system of embodiment 43, wherein the controller controls the first blood pump to generate a flow rate of blood in the processing fluid circuit or in the recirculating blood processing loop that is at least 300 ml/min.

Embodiment 45: The system of embodiment 36, wherein:
- the controller controls the first blood pump to generate a first flow rate of blood in the processing fluid circuit and the second blood pump to generate a second flow rate of blood in the interfacing fluid circuit, and
- the first flow rate is at least 1.25 times greater than the second flow rate.

Embodiment 46: The system of embodiment 45, wherein the first flow rate is at least two times greater than the second flow rate.

Embodiment 47: The system of any one of embodiments 36-46, further comprising a sensor for monitoring at least one of weight, volume, or pressure of the reservoir.

48: The system of embodiment 47, wherein the sensor comprises a gravity scale having an accuracy of 1 g or less.

Embodiment 49: The system of embodiment 36, wherein each of the processing and interfacing fluid circuits comprises one or more valves operatively coupled to the controller.

Embodiment 50: The system of embodiment 49, wherein the controller is configured to control the one or more valves of the interfacing fluid circuit and the second blood pump to deliver at least one of supplemental fluid, anticoagulant, or anticoagulant reversal agent from a respective source to a flowpath in the interfacing fluid circuit.

Embodiment 51: The system of any one of embodiments 36-50, wherein the filtration device or filter comprises a first volume through which blood flows between the blood inlet and the blood outlet, a second volume, and filter structure or membrane separating the second volume from the first volume.

Embodiment 52: The system of embodiment 51, wherein the filtration device or filter is configured as a counter-current flow dialyzer.

Embodiment 53: The system of embodiment 36, further comprising:
- a second processing fluid circuit having another reservoir, another first blood pump, and another filtration device,
- wherein the first conduit of the interfacing fluid circuit is coupled to the another reservoir of the second processing fluid circuit, and
- the controller is configured to control operation of the another first blood pump in performing the extracorporeal treatment.

Embodiment 54: The system of any one of embodiments 36-53, further comprising:
- an infusion device coupled to the first conduit and constructed to infuse a fluid or drug into the patient,
- wherein the controller is configured to send a signal to the infusion device to pause infusion during withdrawal of blood from the patient.

Embodiment 55: A body fluid treatment system comprising:
- a reservoir for holding a batch of body fluid from a patient;
- a first conduit for conveying body fluid from an access of the patient during a first stage and for returning treated body fluid to the access during a third stage, the first conduit having only a single lumen;
- a filter for performing extracorporeal treatment on body fluid passing therethrough by fluid;
- a recirculating processing loop connecting the reservoir to the filter;
- a first pump for conveying body fluid in the recirculating processing loop; and
- a controller configured to control the first pump to recirculate body fluid from the reservoir through the filter during a second stage between the first and third stages.

Embodiment 56: The system of embodiment 55, wherein the extracorporeal treatment is at least one of hemodialysis, hemofiltration, hemodiafiltration, or hemoperfusion.

Embodiment 57: The system of any one of embodiments 55-56, wherein the first conduit is a needle or cannula forming at least part of the access.

58: The system of embodiment 57, wherein the catheter or needle of the first conduit has a size of either 2-11 French or 10-23 gauge.

Embodiment 59: The system of one of embodiments 55-58, wherein the access comprises multiple lumens, and the first conduit is coupled to respective outlets of the multiple lumens by a Y-connector.

Embodiment 60: The system of any one of embodiments 55-59, wherein the reservoir has a volume of 10-300 ml, inclusive.

Embodiment 61: The system of any one of embodiments 55-60, wherein the controller controls the first pump to generate a flow rate of body fluid in the processing fluid circuit or in the recirculating processing loop that is 50-500 ml/min, inclusive.

Embodiment 62: The system of embodiment 61, wherein the controller controls the first pump to generate a flow rate of body fluid in the processing fluid circuit or in the recirculating processing loop that is at least 300 ml/min.

Embodiment 63: The system of embodiment 55, wherein:
the controller controls the first pump to generate a first flow rate of body fluid in the processing fluid circuit and the second pump to generate a second flow rate of body fluid in the interfacing fluid circuit, and
the first flow rate is at least 1.25 times greater than the second flow rate.

Embodiment 64: The system of embodiment 63, wherein the first flow rate is at least two times greater than the second flow rate.

Embodiment 65: The system of any one of embodiments 55-64, further comprising a sensor for monitoring at least one of weight, volume, or pressure of the reservoir.

Embodiment 66: The system of embodiment 65, wherein the sensor comprises a gravity scale having an accuracy of 1 g or less.

Embodiment 67: The system of embodiment 55, wherein each of the processing and interfacing fluid circuits comprises one or more valves operatively coupled to the controller.

Embodiment 68: The system of embodiment 67, wherein the controller is configured to control the one or more valves of the interfacing fluid circuit and the second pump to deliver at least one of supplemental fluid, anticoagulant, or anticoagulant reversal agent from a respective source to a flowpath in the interfacing fluid circuit.

Embodiment 69: The system of any one of embodiments 55-68, wherein the filtration device or filter comprises a first volume through which body fluid flows between the body fluid inlet and the body fluid outlet, a second volume, and filter structure or membrane separating the second volume from the first volume.

Embodiment 70: The system of embodiment 69, wherein the filtration device or filter is configured as a counter-current flow dialyzer.

Embodiment 71: The system of one of embodiments 55-58, wherein the body fluid is a member selected form the group consisting of blood, serum, plasma, lymph, ascites, abdominal fluid, pleural fluid, organ fluid, intestinal fluid or water.

Embodiment 72: The system of embodiments 71, wherein the body fluid ascites.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates the transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine-readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

It is thus apparent that there is provided, in accordance with the present disclosure, extracorporeal blood treatment systems and methods employing batch processing. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

What is claimed is:

1. A blood treatment method comprising:
(a) conveying a volume of blood via a first conduit from a vascular access of a patient to a blood chamber at a first flow rate, the first conduit having only a single lumen, wherein the vascular access comprises multiple lumens, and the first conduit is coupled to respective outlets of one or more of the multiple lumens;

(b) conveying the blood from the blood chamber through a filtration device at a second flow rate to perform an extracorporeal treatment on the blood and returning the treated blood to the blood chamber; and (c) returning the blood from the blood chamber to the vascular access of the patient at a third flow rate via the first conduit, wherein the second flow rate is decoupled from both the first and third flow rates.

2. The method of claim 1, wherein the first conduit is a needle or cannula forming at least part of the vascular access.

3. The method of claim 2, wherein the catheter or needle of the first conduit has a size of either 2-11 French or 10-23 gauge.

4. The method of claim 1, wherein the extracorporeal treatment is at least one of hemodialysis, hemofiltration, hemodiafiltration, or hemoperfusion.

5. The method of claim 1, wherein the volume of blood is 2-7%, inclusive, of a total blood volume of the patient.

6. The method of claim 1, wherein the second flow rate is 50 ml/min-500 ml/min, inclusive.

7. The method of claim 6, wherein the second flow rate is at least 300 ml/min.

8. The method of claim 1, wherein (b) is repeated such that the blood is recirculated more than once through the filtration device via the blood chamber.

9. The method of claim 1, wherein the second flow rate is greater than both the first and third flow rates.

10. The method of claim 9, wherein the second flow rate is at least 1.25 times greater than either of the first flow rate or third flow rate.

11. The method of claim 1, wherein (b) is such that middle molecules contained in the blood are removed via the filtration device.

12. The method of claim 11, wherein:
the first conduit comprises a single-lumen catheter or needle having a size smaller than either 7 French or 17 gauge, and
beta 2 microglobulin clearance is at least 100 ml/min.

13. The method of claim 1, further comprising monitoring a weight of the blood chamber or a volume level of the blood chamber and correlating the monitored weight to a stage of the dialysis process.

14. The method of claim 13, wherein the monitoring occurs simultaneously with the conveying of (b).

15. The method of claim 13, wherein the monitoring occurs during a temporary pause in the conveying of (b).

16. The method of claim 13, wherein the monitoring is via a gravity scale having an accuracy of 1 g or less.

17. The method of claim 1, wherein the first conduit is coupled to respective outlets of the multiple lumens by a Y-connector.

18. A blood treatment method comprising:
(a) conveying a volume of blood via a first conduit from a vascular access of a patient to a blood chamber at a first flow rate, the first conduit having only a single lumen;

(b) conveying the blood from the blood chamber through a filtration device at a second flow rate to perform an extracorporeal treatment on the blood and returning the treated blood to the blood chamber;

(c) monitoring a weight of the blood chamber via a gravity scale having an accuracy of 1 g or less, a volume level of the blood chamber, or a sensor to measure fluid level in the blood chamber and correlating the monitored weight or level to a stage of the dialysis process; and (d) returning the blood from the blood chamber to the vascular access of the patient at a third flow rate via the first conduit, wherein the second flow rate is decoupled from both the first and third flow rates.

19. The method of claim 18, wherein the extracorporeal treatment is at least one of hemodialysis, hemofiltration, hemodiafiltration, or hemoperfusion.

20. The method of claim 18, wherein the second flow rate is greater than both the first and third flow rates.

* * * * *